United States Patent
Loddenkemper et al.

(10) Patent No.: US 10,959,662 B2
(45) Date of Patent: Mar. 30, 2021

(54) SEIZURE PREDICTION USING CARDIOVASCULAR FEATURES

(71) Applicant: Children's Medical Center Corporation, Boston, MA (US)

(72) Inventors: Tobias Loddenkemper, Natick, MA (US); Michele Jackson, Dorchester, MA (US); Fatemeh Mohammadpour Touserkani, Boston, MA (US); Eleonora Tamilia, Cambridge, MA (US); Christos Papadelis, Wakefield, MA (US)

(73) Assignee: Children's Medical Center Corporation, Boston, MA (US)

( * ) Notice: Subject to any disclaimer, the term of this patent is extended or adjusted under 35 U.S.C. 154(b) by 140 days.

(21) Appl. No.: 16/164,706

(22) Filed: Oct. 18, 2018

(65) Prior Publication Data

US 2019/0298248 A1    Oct. 3, 2019

Related U.S. Application Data

(60) Provisional application No. 62/574,044, filed on Oct. 18, 2017.

(51) Int. Cl.
| | |
|---|---|
| *A61B 5/00* | (2006.01) |
| *A61B 5/024* | (2006.01) |
| *A61B 5/026* | (2006.01) |
| *A61B 5/0476* | (2006.01) |

(52) U.S. Cl.
CPC ........... *A61B 5/4094* (2013.01); *A61B 5/026* (2013.01); *A61B 5/02405* (2013.01); *A61B 5/02416* (2013.01); *A61B 5/7275* (2013.01); *A61B 5/0476* (2013.01); *A61B 5/7264* (2013.01)

(58) Field of Classification Search
CPC .............. A61B 5/4094; A61B 5/02405; A61B 5/02416; A61B 5/026; A61B 5/7275; A61B 5/0476; A61B 5/7264
USPC ......................................................... 600/301
See application file for complete search history.

(56) References Cited

U.S. PATENT DOCUMENTS

| | | | | |
|---|---|---|---|---|
| 2010/0268056 | A1* | 10/2010 | Picard | A61B 5/6807 600/388 |
| 2015/0272494 | A1* | 10/2015 | Fuerst | A61N 1/37258 600/301 |
| 2016/0367157 | A1* | 12/2016 | Blake | A61B 5/0428 |

FOREIGN PATENT DOCUMENTS

WO    WO 2017/007808 A1    1/2017

OTHER PUBLICATIONS

Allen, Photoplethysmography and its application in clinical physiological measurement. Physiol. Meas. 2007;29:R1-39.

(Continued)

*Primary Examiner* — Erin M Piateski
(74) *Attorney, Agent, or Firm* — Melissa Hunter-Ensor; Kristopher Reichten; Greenberg Traurig, LLP

(57) ABSTRACT

An apparatus for generating a prediction that a patient will experience a seizure based on a blood volume signal is provided. The apparatus may include a blood volume sensor to sense the blood volume in a location of a patient's body. The apparatus may extract one or more features from the blood volume signal and determine if the feature has changed over time. The apparatus may generate a prediction of whether the patient will experience a seizure based on the determination of whether the feature changed over time.

20 Claims, 20 Drawing Sheets

(56) References Cited

OTHER PUBLICATIONS

Balasubramanian et al., A robust and sensitive metric for quantifying movement smoothness. IEEE Trans Biomed Eng. 2012;59(8):2126-36.

Bartels et al. Advances in photoplethysmography: Beyond arterial oxygen saturation. Can J Anaesth. Dec. 2015;62(12):1313-28. doi: 10.1007/s12630-015-0458-0. Epub Aug. 19, 2015.

Fujiwara et al., Epileptic Seizure Prediction Based on Multivariate Statistical Process Control of Heart Rate Variability Features. IEEE Transactions on Biomedical Engineering. 2016;63(6):1321-32.

Goldman, Mechanisms of sudden unexplained death in epilepsy. Curr Opin Neurol. Apr. 2015;28(2):166-74. doi: 10.1097/WCO.0000000000000184.

Golestani et al., Can we predict the unpredictable? Sci Rep. Oct. 30, 2014;4:6834. doi: 10.1038/srep06834. 6 pages.

Haut et al., Modeling seizure self-prediction: an e-diary study. Epilepsia. Nov. 2013;54(11):1960-7. doi: 10.1111/epi.12355. Epub Sep. 20, 2013.

Hofstra et al. The circadian rhythm and its interaction with human epilepsy: a review of literature. Sleep Med Rev. Dec. 2009;13(6):413-20. doi: 10.1016/j.smrv.2009.01.002. Epub Apr. 24, 2009.

Kamal, Assessment of autonomic function in epileptic patients. Neurosciences (Riyadh). Oct. 2010;15(4):244-8.

Lotufo et al., A systematic review and meta-analysis of heart rate variability in epilepsy and antiepileptic drugs. Epilepsia. Feb. 2012;53(2):272-82. doi: 10.1111/j.1528-1167.2011.03361.x. Epub Jan. 5, 2012.

Papadelis et al., Real-time multi-channel monitoring of burst-suppression using neural network technology during pediatric status epilepticus treatment. Clinical Neurophysiology. 2016;127:28200-2831.

Ramgopal et al., Seizure detection, seizure prediction, and closed-loop warning systems in epilepsy. Epilepsy Behav. Aug. 2014;37:291-307. doi: 10.1016/j.yebeh.2014.06.023. Epub Aug. 29, 2014.

Schiecke et al., Time-Variant, Frequency-Selective, Linear and Nonlinear Analysis of Heart Rate Variability in Children With Temporal Lobe Epilepsy. IEEE Trans Biomed Eng. Jun. 2014;61(6):1798-808. doi: 10.1109/TBME.2014.2307481.

Tamilia et al., An Automated System for the Analysis of Newborns' Oral-Motor Behavior. IEEE Transactions on Neural Systems and Rehabilitation Engineering. 2015;25(12):1294-1303.

Tamilia et al., An Automatized System for the Assessment of Nutritive Sucking Behavior in Infants: a Preliminary Analysis on Term Neonates. IEEE Eng Med Biol Soc. 2014;5752-5.

Van Elmpt et al., A model of heart rate changes to detect seizures in severe epilepsy. Seizure. Sep. 2006;15(6):366-75. Epub Jul. 7, 2006.

\* cited by examiner

SEIZURE PREDICTION USING CARDIOVASCULAR FEATURES

RELATED APPLICATIONS

This application claims the benefit under 35 U.S.C. § 119(e) of U.S. Provisional Patent Application Ser. No. 62/574,044 filed on Oct. 18, 2017, entitled "SEIZURE PREDICTION BASED ON CARDIOVASCULAR FEATURES" the entire contents of which are incorporated by reference herein.

BACKGROUND

Epilepsy affects approximately 0.5% to 0.8% of the world population. Epilepsy often leads to a poor quality of life for patients in part because seizures cannot be reliably predicted and, in extreme cases, are associated with sudden unexpected death in epilepsy (SUDEP). Seizure detection prior to the onset of a seizure could reduce the risk of injuries to a patient, improve treatment and possibly prevent SUDEP.

Existing methods to predict seizures focus principally on analysis of brain electrical activity by electroencephalogram (EEG) or invasive monitoring.

SUMMARY

According to one aspect of the present application, an apparatus is provided. The apparatus may include at least one first sensor to measure blood volume at a location within a patient; at least one processor; and at least one storage having encoded thereon executable instructions that, when executed by the at least one processor, cause the at least one processor to perform a method. The method may include: monitoring a blood volume signal received from the at least one sensor; extracting at least one feature from the blood volume signal at a plurality of times; determining a change in the at least one feature over time; and generating a prediction of whether the patient will experience a seizure at a future time based at least in part on a result of the determining.

According to another aspect of the present application, a system to predict occurrence of seizures in a monitored individual is provided. The system may include: at least one storage medium containing data defining at least one biological characteristic of the monitored individual. The data defining at least one biological characteristic of the monitored individual may include measurement results take over a time period. The at least one biological characteristic may include a blood volume at a location within the monitored individual. The system may also include a computer server coupled to the computer store and programmed to: extract at least one feature from the data at a plurality of times; determine a change in the at least one feature over time; and generate a prediction of whether the patient will experience a seizure at a future time based at least in part on the determined change.

According to another aspect of the present application, a method is provided. The method may include determining a change in at least one feature extracted from a photoplethysmography (PPG) measurement of a patient; and generating a prediction of whether the patient will experience a seizure at a future time based at least in part on a result of the determining.

According to another aspect of the present application, at least one non-transitory storage medium encoded with executable instructions that, when executed by at least one processor, cause the at least one processor to carry out a method of analyzing data associated with a photoplethysmography (PPG) measurement is provided. The method may include determining a change in at least one feature extracted from a photoplethysmography (PPG) measurement of a patient; and generating a prediction of whether the patient will experience a seizure at a future time based at least in part on a result of the determining.

According to another aspect of the present application, a system to predict seizure occurrence in a monitored individual is provided. The system may include: at least one processor; and at least one storage medium having encoded thereon executable instructions that, when executed by the at least one processor, cause the at least one processor to carry out a method. The method may include determining a change in at least one feature extracted from a photoplethysmography (PPG) measurement of a patient; and generating a prediction of whether the patient will experience a seizure at a future time based at least in part on a result of the determining. The foregoing summary is to be considered non-limiting.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
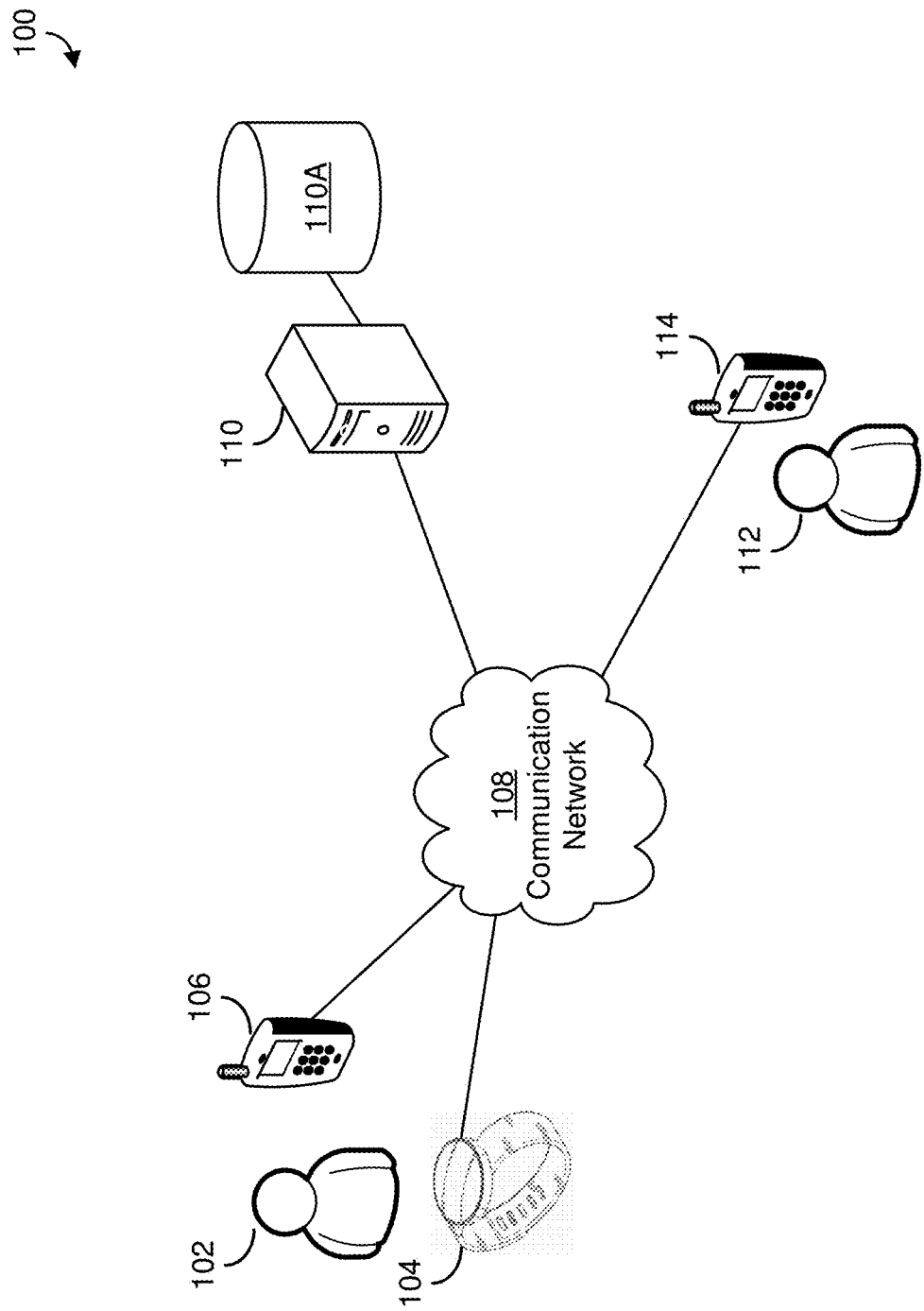
FIG. 1 is a diagram of illustrative components of a computer system with which some embodiments may operate.

Described herein are embodiments of a method and a device used to predict the occurrence of seizures for a patient (e.g., a human or animal) based on biological information for the patient. Such a device may, for example, be able to predict seizures up to ten minutes in advance of a seizure. For example, a seizure may be predicted up to one minute, up to two minutes, up to five minutes, or up to ten minutes in advance of a seizure. In response to such a prediction, the device may notify a caretaker or some other user, such as the patient himself, that a seizure is likely to occur. The notification allows the caretaker and/or patient to prepare for the seizure by ensuring the safety of the patient.

The inventors have recognized and appreciated that patients would benefit greatly from a reliable way of predicting whether a person will have a seizure in a particular time period. Several techniques have been proposed for seizure detection, which may include informing epilepsy patients or caregivers of a seizure that is currently in progress or is imminent. However, techniques for seizure prediction are not readily available. The inventors have recognized and appreciated that, due to the danger inherent in epilepsy, it would be helpful to patients and caregivers to be able to predict the occurrence of a seizure, such as by determining whether a seizure may occur beyond a few seconds following the prediction, such as minutes or tens of minutes following the prediction. This may give the epileptic patient or a caregiver the ability to plan for the seizure, such as through the patient avoiding placing themselves in a situation in which a seizure may injure others (e.g., driving a car) or through the caregiver keeping a closer watch on the patient.

The inventors have recognized and appreciated that there are various disadvantages to existing techniques for seizure prediction. Existing techniques focus on predicting seizures using electroencephalograms (EEGs), or more invasive monitoring of the brain. EEGs require a great deal of data regarding electrical activity within a patient's brain and require the placement of many sensors around the patient's skull and often the application of a conductive gel. Such a procedure is difficult to perform over a long term. The EEG is not designed to be freely mobile, to be used as patients go about their lives, and many patients may feel uncomfortable wearing an EEG monitor for an extended period of time. Moreover, many EEG techniques are only able to generate a reliable prediction of a seizure that applies to a few seconds or minutes following the prediction. The inventors have therefore recognized and appreciated that it would be advantageous to patients to have a device that is non-intrusive and may be used or worn as the patients move through a normal daily routine, and the advantages of a device that generates a reliable prediction of whether a patient will experience a seizure over the course of minutes following generation of the prediction.

The inventors have further recognized and appreciated that measurement of blood volume within a patient may be used to predict a seizure at a future time. Before, during, and after a seizure the function of the autonomic nervous system (ANS) changes. The ANS controls blood pressure and cardiac output, which are determining factors for vascular tone and blood flow. Accordingly, the inventors have recognized and appreciated that a measurement of blood volume and blood flow in vessels of a patient may reflect the changes in the ANS function.

In some embodiments, the blood volume of blood circulating through the microvasculature of a patient is measured using a photoplethysmography (PPG) sensor (sometimes referred to as a photoplethysmograph). A PPG sensor may include a light source that radiates light into the underlying tissue and a photodetector that detects the reflected light from the tissue. In some PPG sensors, as a blood volume increases in the underlying vessels, an amplitude of a signal generated by a photodetector decreases because the amount of absorbed light increases, and thereby the photodetector receives less reflected light from the underlying tissue. Changes in this signal over time may be used in some embodiments to determine a prediction of future seizure occurrence.

Accordingly, examples are described below of techniques for generating a prediction of seizure occurrence and of devices for use with such techniques. In some embodiments, a blood volume signal measurement of a patient may be monitored with a sensor and at least one feature is extracted from a blood volume signal received from the sensor. Such a measurement of blood volume may be a measurement of blood volume at one or more times, such as times associated with a pulse or other times. A time associated with a pulse may be a high point of pressure or volume in a monitored blood vessel. As used herein, a "blood volume signal" may be a "pulse blood volume signal" associated with such a high point of pressure or volume for a pulse, or may be a measurement of volume at another time. One or more changes in the at least one feature over time may also be determined. A prediction of whether the patient will experience a seizure is then generated based, at least in part, on a result of the change(s). In some illustrative embodiments, the first sensor is a PPG sensor. In some illustrative embodiments, a PPG signal is combined with measurements made by other sensors to make the prediction. In some embodiments, an apparatus including the sensor, a memory and a processor may be worn by the patient. In other embodiments, the sensor may be worn by the user, but transmit the data to a separate computing system for analysis.

In some embodiments, the blood volume signal may be analyzed to identify individual pulses within the blood volume signal. In some embodiments, one or more features are extracted from each pulse within the blood volume signal. The one or more features are observed over time to determine whether one or more of the features changes by an amount that is greater than a threshold. For example, a current extracted feature may be compared to a baseline feature measurement of the extracted feature. When a difference between the current extracted feature and the baseline feature measurement is greater than a threshold, a prediction that the patient will experience a seizure at a future time may be generated.

Various illustrative examples of techniques for seizure prediction, and devices for detecting cardiovascular conditions of a patient and generating a prediction of onset of a seizure based on the cardiovascular conditions, are described below. It should be appreciated, however, that embodiments are not limited to operating in accordance with any of the examples below, and that other embodiments are possible.

FIG. 1 illustrates an example of a system with which some embodiments may operate. In the computer system 100 of FIG. 1, a patient 102 operates a wearable device 104 and a computing device 106. The wearable device 104 is illustrated in FIG. 1 as a wristlet that is shaped and arranged to be worn on and attached to a wrist of the patient 102. It should be appreciated, however, that embodiments are not limited to operating with a wearable device that is arranged to be worn at any particular location on the body and embodiments may instead operate with a wearable device that may be worn at any suitable location on the body. For example, the wearable device 104 may be worn on a portion of an arm (e.g., a shoulder, an upper arm (bicep), a forearm, or a wrist), a portion of a leg (e.g., a thigh, a calf, or an ankle), an ear, a forehead, a neck, a chest, a toe, a foot, a hand, or a finger of the patient.

The wearable device 104 may include one or more sensors to collect information that may be analyzed to generate a prediction of whether the patient 102 will experience a seizure. For example, in some embodiments the wearable device 104 may include a PPG sensor. In some embodiments, the wearable device may additionally include a pulse sensor, a thermometer, an electrodermal activity sensor, a motion sensor, an electrocardiograph, and/or one or more sensors to detect a body temperature of the patient 102. The wearable device 104 may include a storage to store data collected by the sensor(s).

In some embodiments, the wearable device 104 may include one or more processors or other control circuits configured or programmed to analyze the data generated by the one or more sensors and to generate a prediction of whether the patient will experience a seizure. For example, the wearable device 104 may store and execute a seizure prediction facility to generate the prediction. Upon generating the prediction, the wearable device 104 may output the prediction via a user interface of the device 104, such as via a display screen, a light (e.g., a light-emitting diode (LED)), a speaker, a vibration circuit, and/or other form of output. In some embodiments, the wearable device 104 may additionally or alternatively transmit the prediction, together with any other suitable information, to the computing device 106 for output, such as via wired and/or wireless transmission components of the wearable device 104. The prediction may be communicated to the device 106 in any suitable manner, including as a voice message, a text message (e.g., SMS message), an email, or other message. For example, the computing device 106 may be implemented as a mobile device such as a smartphone, and the device 104 may transmit the prediction to the mobile device, such as to an "app" implemented on the smart phone, to present the prediction to the patient 102. The computing device 106 is illustrated in FIG. 1 as a smartphone, but it should be appreciated that in embodiments other forms of computing devices may be used, such as laptop or desktop personal computers, personal digital assistants (PDAs), or other devices. In such embodiments, the wearable device 104 may transmit the data via a communication network 108, discussed below.

In some embodiments, the wearable device 104 (and/or the device 106) may also transmit the data from the one or more sensors to one or more servers 110. The device 104 may transmit the information to the server(s) 110 over the communication network 108. The server(s) 110 may be implemented as any suitable computing device or array of computing devices, as embodiments are not limited in this respect. For example, the server(s) 110 may be a distributed network of servers, a desktop or laptop personal computer, a mobile device, or other computing device to analyze data. In some embodiments, the server(s) 110 may be implemented as a mobile device operated by the patient 102, and may be the same device as the device 106. In other embodiments, the server(s) 110 may be operated by a medical care provider, such as a doctor's office, or by a provider of a seizure prediction service, and may be located remote from the patient 102.

Server(s) 110 may be configured to store the received information in a data store 110A. Information may be stored in the data store 110A in association with an account for the patient 102 or otherwise in association with information identifying the patient 102 to indicate that the information relates to patient 102. In some embodiments, the server(s) 110 may additionally relay information, including the prediction, to other devices that have been associated (e.g., through prior configuration input) in the data store 110A with the patient 102. For example, the data store 110A may store information indicating that the patient 102 is associated with the device 104, the device 106, and/or the device 114 (e.g., via an association between the patient 102 and the caregiver 112). In response to identifying that association, the server(s) 110 may relay information to one or more of those devices.

In some embodiments, the wearable device 104 (and/or device 106) may not be configured to analyze data to generate a prediction of whether the patient 102 will experience a seizure. Instead, in some such embodiments, the server(s) 110 may include one or more processors or other control circuits to analyze the data and generate the prediction. For example, the server(s) 110 may store and execute a seizure prediction facility to generate the prediction. In such embodiments, the server(s) 110 may store the prediction in the data store 110A and may transmit the prediction to the wearable device 104 and/or the device 106 for output to the patient 102. In such embodiments, the server(s) 110 may transmit the prediction via the communication network 108.

In some embodiments in which the server 110 is separate from the device 106, instead of or in addition to a server 110 receiving the sensor data from the wearable device 104, storing the sensor data, executing a seizure prediction facility to analyze the data to generate a prediction, and transmitting the prediction to the wearable device 106 for output, the device 106 may be configured to perform one or more of these functions, including by storing and executing the seizure prediction facility and/or by relaying communications (including data and/or seizure predictions) between the device 104 and server 110.

In some embodiments, the wearable device 104, the device 106, and/or the server(s) 110 may additionally communicate to a caregiver 112 the prediction of whether the patient 102 will experience a seizure. Caregiver 112 may be a person who may care for the patient 102, such as a friend or family member of patient 102 or a medical professional such as a doctor or nurse. In some such embodiments, the device 104, device 106, and/or server(s) 110 may transmit the prediction, via the communication network 108, to a device 114 operated by the caregiver 112. The device 114 may be any suitable computing device, as embodiments are not limited in this respect. The prediction may be communicated to the device 114 in any suitable manner, including as a voice message, a text message (e.g., SMS message), an email, or other message. For example, the computing device 114 may be implemented as a mobile device such as a smartphone, and the device 104 may transmit the prediction to the mobile device, such as to an "app" implemented on the smart phone, to present the prediction to the caregiver 112. The computing device 114 is illustrated in FIG. 1 as a smartphone, but it should be appreciated that in embodiments other forms of computing device may be used, such as laptop or desktop personal computers, personal digital assistants (PDAs), or other devices.

The communication network 108 by which the devices of system 110 may communicate may be or include one or more wired and/or wireless networks. In some embodiments, the network 108 may include one or more wireless personal area networks (WPAN), one or more wireless and/or wired local area networks (LANs), and/or one or more wireless and/or wired wide area networks (WANs), and in some embodiments may include the Internet.

Figure 2:
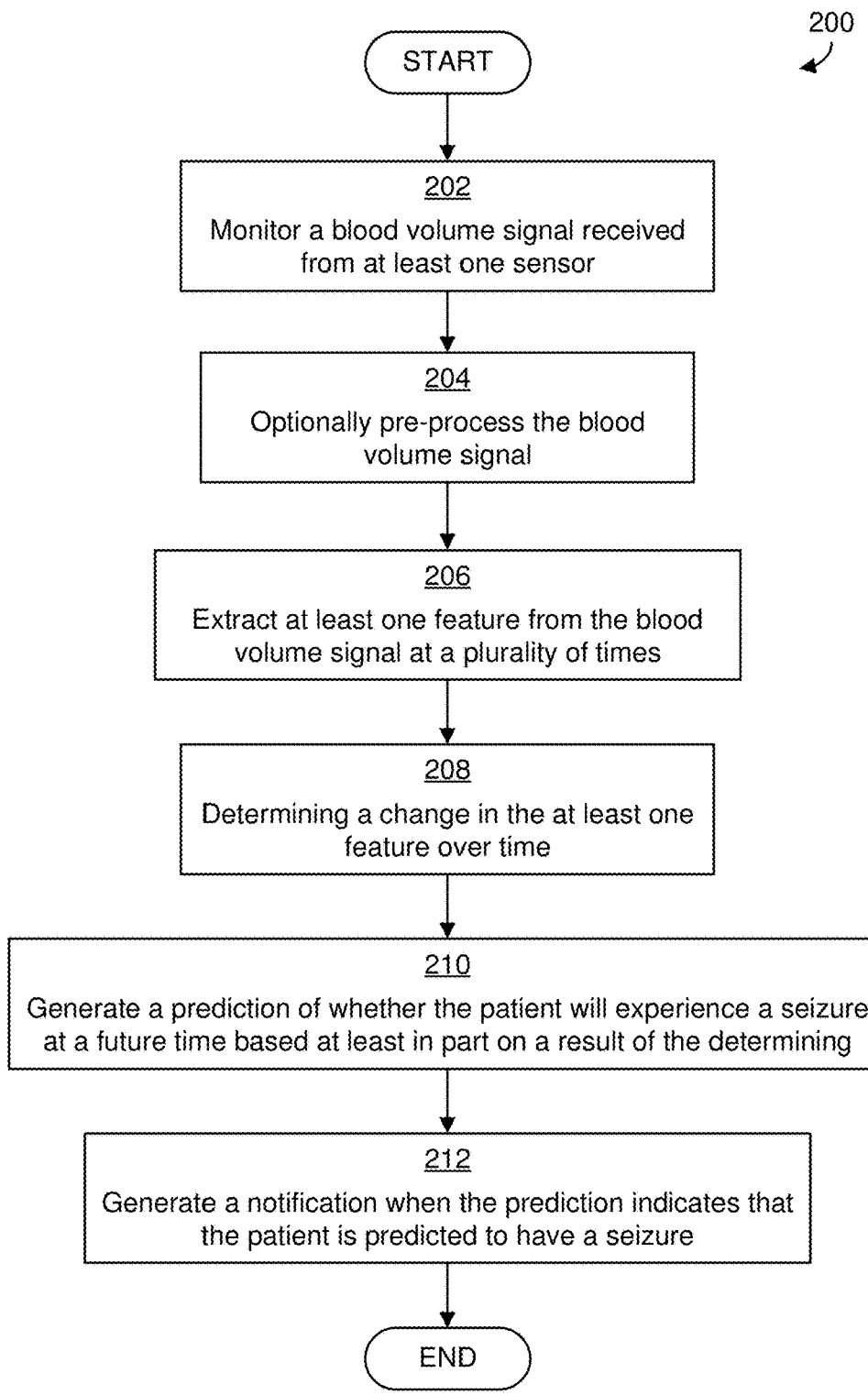
FIG. 2 is a flowchart of an example of a method that some embodiments may implement to predict occurrence of a seizure.
Figure 3:
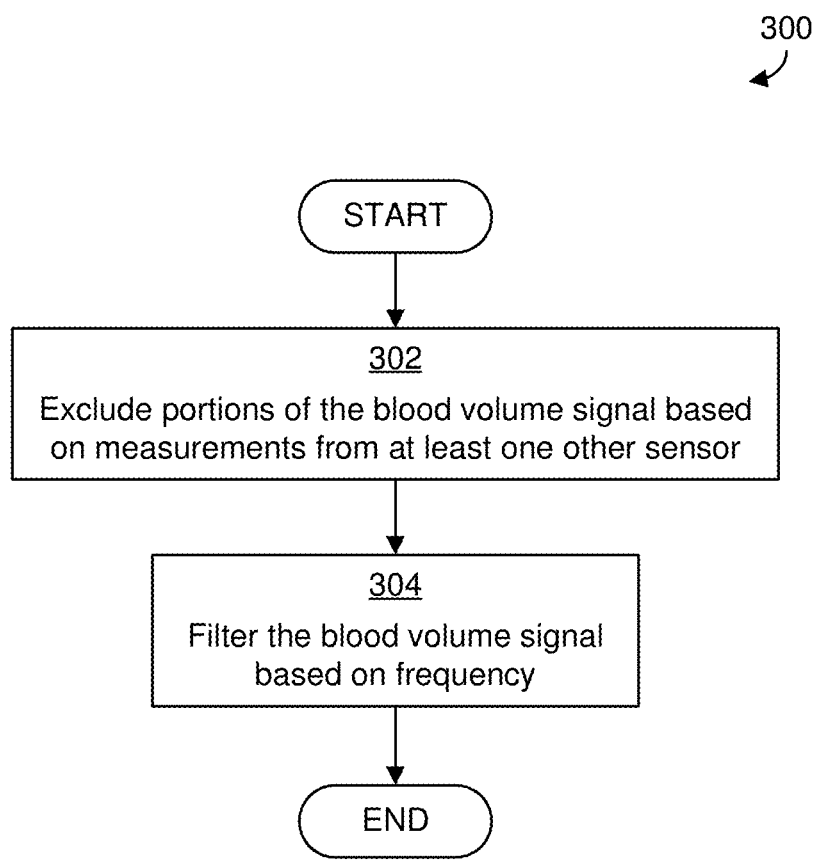
FIG. 3 is a flowchart of an example of a method that some embodiments may implement to pre-process a blood volume signal.
Figure 4:
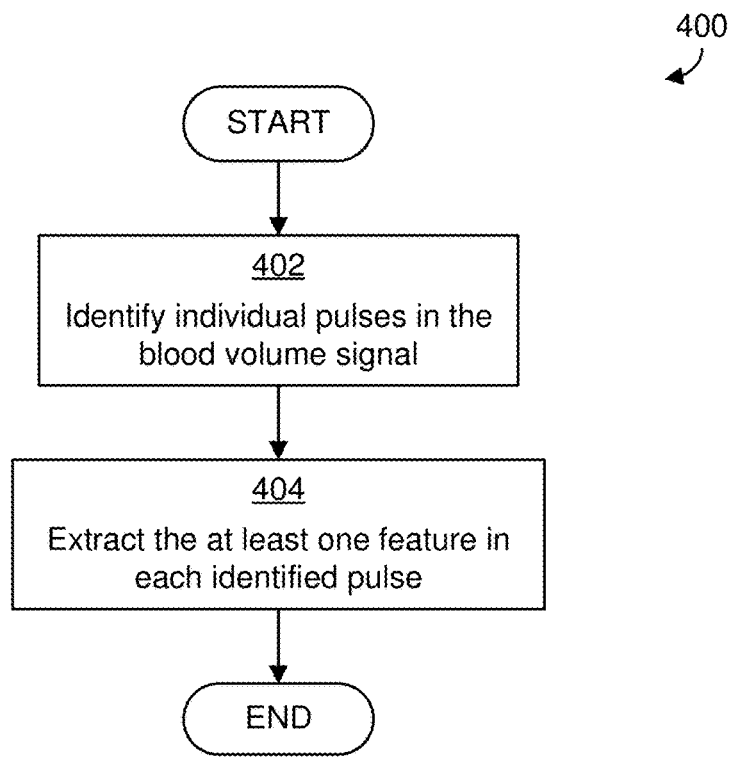
FIG. 4 is flowchart of an example of a method that some embodiments may implement to extract features from a blood volume signal.

As discussed above, in some embodiments a device (e.g., wearable device 104 and/or server(s) 110) may execute a seizure prediction facility that analyzes biological information for a patient and generates a prediction of whether the patient will experience a seizure. FIGS. 2-4 illustrate examples of methods/processes that may be implemented by a device according to some embodiments.

Referring to FIG. 2, a method 200 of predicting seizures in a patient includes multiple blocks. In some embodiments, certain blocks shown in FIG. 2 may not be performed. In some embodiments, additional blocks that are not shown in FIG. 2 may be included in the method 200. Additionally, the order of the blocks in method 200 are not limiting. Some embodiments may perform the blocks of method 200 in a different order than that shown in FIG. 2. For example, multiple blocks may be performed simultaneously.

The process 200 begins in block 202, in which at least one sensor and/or a seizure prediction facility monitors a blood volume signal generated by the sensor(s). For example, a patient may be wearing a wearable device incorporating the sensor(s) and the sensor(s) may be monitoring the blood volume and other biological characteristics and generating signal. The signal may take the form of data transmitted by the sensor(s) in any form. The signal may be an analog signal or a digital signal. For example, the data generated by the sensor(s) may include values for biological characteristics that the sensors generated continuously and/or at discrete sampling intervals (e.g., multiple times a second, every minute, every few minutes, several times an hour, or any other suitable interval) and each value may be associated with a time the value was generated. The time may be an absolute time, such as a time of day and/or date, or may be an elapsed time from a reference point such as a start of monitoring, or may be any other suitable time.

In block 204, the sensor and/or the seizure prediction facility pre-processes the blood volume signal. Pre-processing may occur to the signal from the sensor while the sensor is in analog form, after conversion to a digital format, or both. By pre-processing the signal, unwanted data may be removed from the blood volume signal, thereby increasing the accuracy of the seizure prediction.

The pre-processing may take any suitable form, as embodiments are not limited in this respect. FIG. 3 illustrates one method for performing the pre-processing of block 204, according to some embodiments. In block 302, the portions of the blood volume signal may be excluded based on measurements from at least one other sensor. By way of example and not limitation, the blood volume signal from a PPG sensor may become unreliable when the patient moves a part of the body that includes the location the PPG sensor is measuring. Therefore, it may be advantageous to exclude portions of the blood volume signal that correspond to times when the patient was moving. This can be achieved using measurements made by a motion sensor, such as one or more accelerometers. In some embodiments, data from one or more accelerometers includes timing information that can be correlated with the timing information from the PPG sensor. By correlating the accelerometer data with the PPG sensor data, the seizure prediction facility can exclude the portions of the blood volume signal that were acquired while the patient was moving. In some embodiments, portions of the blood volume signal may only be excluded if the motion of the patient exceeds a threshold level of movement.

In block 304, the blood volume signal is filtered based on frequency. A PPG signal may include a zero-frequency component (what might be thought of as a "direct current" ("DC") component) and one or more other components having non-zero frequencies (what might be thought of as an "alternating current" ("AC") portion). The AC component results from changes in tissue blood volume during each systole and reflects changes in the micro-vascular perfusion relative to each heartbeat. The DC component is less variable and results from the average blood volume in the tissue resulting from respiration, vasomotor activity and thermo-regulation. In some embodiments, between the two components, the component of the blood volume signal that is more reflective of, or most impacted by, changes in the ANS, and therefore most indicative of a possible seizure, is the AC component. Accordingly, in some embodiments, the frequency-based filter used to filter the blood volume signal may be a bandpass filter used to filter out the DC component and high frequency components of the blood volume signal. In some embodiments, the bandpass filter may pass frequencies that range from 0.1 to 20 Hz, 0.1 to 10 Hz, 0.1 to 8 Hz, or 0.1 to 5 Hz. In some embodiments, a Butterworth filter is also used to maintain a flat frequency response.

In some embodiments, the order of blocks 302 and 304 may be reversed such that the frequency-based filtering of block 304 is performed before the excluding acts of block 302. In other embodiments, one or both of blocks 302 and 304 may be omitted.

Referring back to FIG. 2, in block 206 the seizure prediction facility extracts at least one feature from the blood volume signal at a plurality of times. In some embodiments, each of the plurality of times may include a specific time period. For example, a time period may be on the order of a fraction of a second, one to two seconds or many seconds. In some embodiments, each of the plurality of times may be a time period defined by the blood volume signal itself. For example, each systole creates a pulse in a blood volume signal. One or more features may be extracted from each pulse in the blood volume signal and each pulse can be associated with a start time of the pulse, an end time of the pulse, or a median time of the pulse.

FIG. 4 illustrates a method for performing the extracting block 206, according to some embodiments. In block 402, individual pulses in the blood volume signal (e.g., a PPG signal) are identified by the seizure prediction facility. The identification of individual pulses may be done in any suitable way. In some embodiments, an automatic threshold-based detection technique may be used. One such detection technique is described in the article by Tamilia, E., et al., *An Automated System for the Analysis of Newborns' Oral-Motor Behavior*, published in IEEE Transactions on Neural Systems and Rehabilitation Engineering, Vol. 25, No. 12, December 2015 ("Tamilia-1"), which is incorporated herein by reference in its entirety and at least for its discussion of an automatic threshold-based detection technique. (In a case that any terminology used herein conflicts with the usage of that terminology in Tamilia-1, the terminology should be afforded a meaning most consistent with how a person of ordinary skill would understand its usage herein.) In some embodiments, a local maxima of the PPG signal is identified as a peak associated with a pulse. A threshold may be used to ensure identified local maxima actually correspond to a maximum of a pulse. In some embodiments, the minimum between two identified local maxima are then identified. Each local minima is identified as the start of a pulse and the local minimum subsequent to a particular local minimum is identified as the end of the pulse. In some embodiments, a start time and a stop time is identified for each individual pulse in the PPG signal.

In block 404, at least one feature is extracted from each identified pulse. Examples of possible features that may be extracted from an individual pulse of the PPG signal include, but are not limited to:

(i) Period (P), as determined by the time between two consecutive pulse peaks (measured in seconds);
(ii) Frequency (F), as determined by the inverse of the time between two consecutive pulse peaks (measured in Hz);

(iii) Peak amplitude (A), as determined by the difference between the PPG signal value at the start of the pulse and the identified local maximum associated with the pulse (measured in nW);
(iii) Duration (D), as determined by the difference between the start time and the end time of the pulse (measured in seconds);
(iv) Increasing slope (IS), i.e., the slope of the increasing phase of the PPG pulse, as determined by the slope of the linear line between the pulse start and the identified local maximum associated with the pulse (measured in nW/sec). In some embodiments, this may be calculated as the ratio between the peak amplitude and the time duration between the start of the pulse and the peak;
(v) Decreasing slope (DS), i.e., the slope of the decreasing phase of the PPG pulse, as determined by the slope of the linear line between the identified local maximum associated with the pulse and the pulse end (measured in nW/sec). In some embodiments, this may be calculated as the ratio between the peak amplitude and the time duration between the peak and the end of the pulse;
(vi) Smoothness of the pulse, calculated using, e.g., the spectral arc-length metric described by Balasubramanian, S., A. Melendez-Calderon, and E. Burdet, *A robust and sensitive metric for quantifying movement smoothness.* IEEE Trans Biomed Eng, 2012. 59(8): p. 2126-36 ("Balasubramanian"), which is incorporated by reference in its entirety and at least for its discussion of the spectral arc-length technique for calculating pulse smoothness (in a case that any terminology used herein conflicts with the usage of that terminology in Balasubramanian, the terminology should be afforded a meaning most consistent with how a person of ordinary skill would understand its usage herein);
(vii) Area under the curve (AUC), calculated between the start of the pulse and the end of the pulse using, e.g., the trapezoidal rule (measured in nW·sec)

In some embodiments, the aforementioned features may be extracted from the PPG signal using techniques described in Tamilia-1 and an article by Tamilia, E., et al., *An automatized system for the assessment of nutritive sucking behavior in infants: a preliminary analysis on term neonates*, published in Conference Proceedings of the IEEE Eng Med Biol Soc, 2014. 2014: p. 5752-5 ("Tamilia-2"), which is incorporated herein by reference in its entirety and at least for its discussion of the techniques for extraction of features from a signal. (In a case that any terminology used herein conflicts with the usage of that terminology in Tamilia-2, the terminology should be afforded a meaning most consistent with how a person of ordinary skill would understand its usage herein.)

Figure 5:
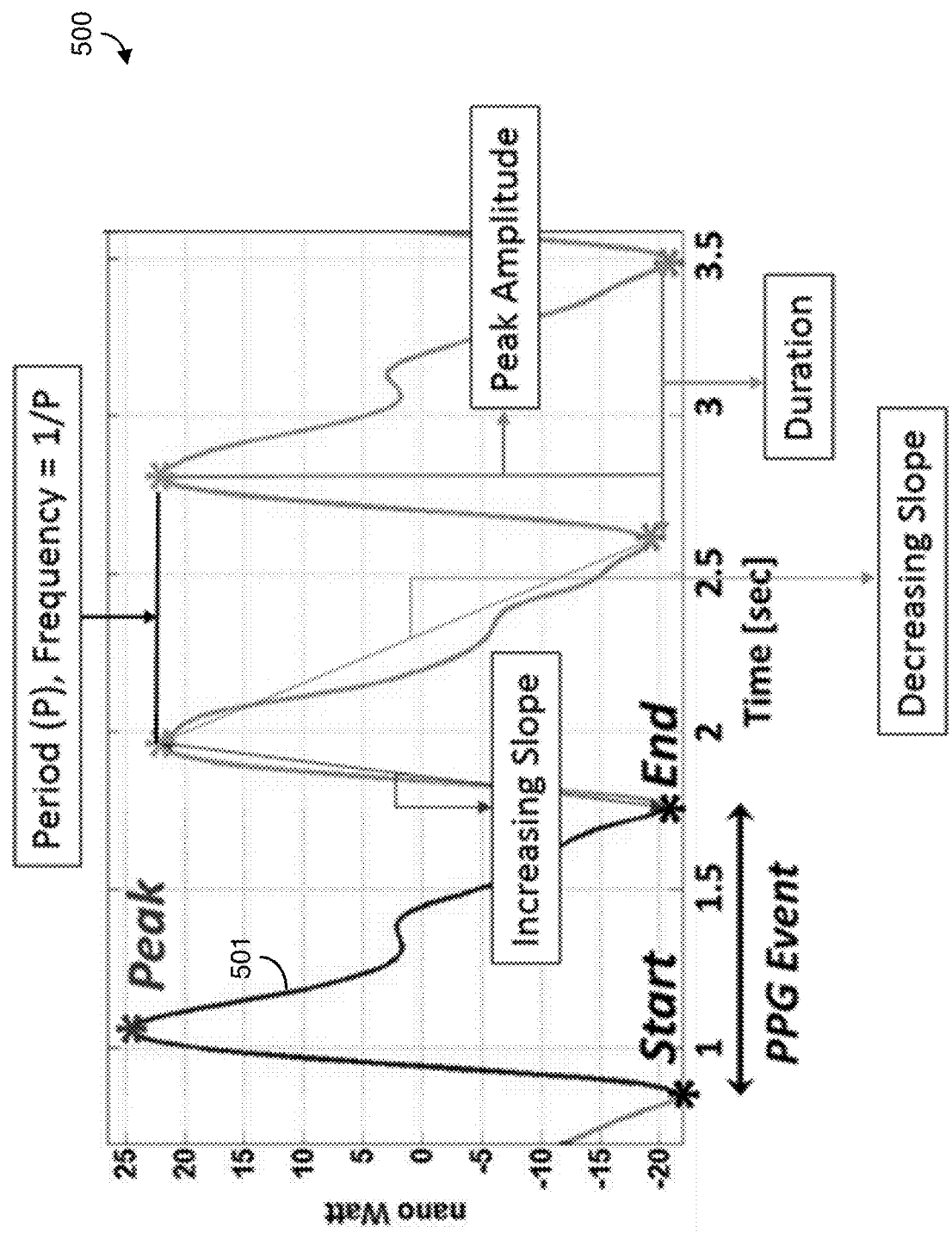
FIG. 5 is a plot of an example blood volume signal with three pulses.

FIG. 5 is a plot 500 of an example PPG signal 501 (measured in nanowatts) as a function of time (measured in seconds). Several of the above-mentioned extracted features are labeled in FIG. 5. Note that the value of the PPG signal 501 at the start and end of a particular pulse (also referred to as a PPG event) may be different. As a result, some embodiments may calculate the above features in slightly different ways. For example, the peak amplitude may be calculated using the value of the PPG signal 501 at the start of the pulse, the end of the pulse, or an average of the two values.

As is described below in connection with experimental results, some of the above features may be, by themselves, more predictive of seizures than other features by themselves. In some embodiments, the frequency, the duration, and the area under a curve associated with each pulse may be solely used to generate a prediction of whether the patient will experience a seizure. In other embodiments, a combination of two or all of the frequency, the duration, and the area under a curve associated with each pulse may be used. Though, in other embodiments, any one or any combination of the features discussed above, or other features extracted from a PPG signal, may be used to predict occurrence of a seizure.

Referring back to FIG. 2, the method 200 includes block 208 in which a change in the at least one factor over time is determined. In some embodiments, a baseline measurement of a feature is used to determine that a change in the feature has occurred. For example, the seizure prediction facility may determine that the difference between a current value of the feature and the baseline value of the feature is greater than a threshold. In some embodiments, the difference between a current value of the feature and a baseline value must be greater than the threshold for a predetermined number of consecutive current values before it is determined that a change in the factor has occurred. In other embodiments, the facility may instead determine whether one or more statistical values derived from a number of current feature values over time (e.g., a moving average, or a slope or other change over time in the current feature values) exceeds a threshold, to determine whether a change in the factor has occurred. In some embodiments, a combination of a comparison between a current value and a threshold, and a comparison between a statistical value derived from a number of current feature values over time, may be used by the facility, such as in a weighted combination using any suitable weights.

In some embodiments, the baseline value is based at least in part on one or more PPG measurements made on the patient. In some embodiments, the baseline value may be based on PPG measurements made at during a time period more than 30 minutes, one hour, or two hours before a current time, as long as the patient has not had a seizure during that time period. In some embodiments, the baseline value may be based on PPG measurements made at during a time period less than five hours before the current time. The baseline value may be a statistical value, such as a mean or median, based on features extracted from a plurality of PPG pulses that occur in a time period as defined above. For example, the baseline may be the average value of a feature for 100, 200, 300 or 500 PPG pulses that occurred one hour before the current time.

In some embodiments, the threshold value is also based at least in part on one or more PPG measurements made on the patient. For example, a statistical value, such as a standard deviation, may be calculated based on the values of a feature for a number of PPG pulses that occur in a time period before the current time. The time period may correspond to the same time period used to determine the baseline. For example, a standard deviation of a feature for 100, 200, 300 or 500 PPG pulses that occurred one hour before the current time feature may be determined for 100, 200, 300 or 500 PPG pulses that occurred one hour before the current time. In some embodiments, the threshold may be proportional to the standard deviation of that feature. For example, the threshold may be 0.5, 1.0, 1.5, 2.0, or 2.5 standard deviations above the average value of the feature.

In block 210, the seizure prediction facility generates, based on a result of the determining, a prediction of whether a patient will experience a seizure at a future time. In some embodiments, the facility may output a "yes" prediction, indicating a potential seizure, when the change in a feature is indicative of a seizure, or a "no" prediction otherwise. In other embodiments, the facility may generate a likelihood of a seizure, including a numeric likelihood, a low/medium/high likelihood or other qualitative prediction, or other relative value indicating a chance of a seizure occurring. In some embodiments, to generate the prediction, the seizure prediction facility may be configured with definitions corresponding to various predictions, such as definitions for "yes" and "no" predictions or definitions for "low," "medium," and "high" predictions. The definition may be, for example, one or more conditions to be satisfied, such as a threshold. In such embodiments, the facility may evaluate the result of the determining of block 208 with respect to the condition(s) for each prediction to determine whether the result of the comparison satisfies a definition for a prediction. When the result satisfies a definition for a prediction, the seizure prediction facility generates that prediction.

In some embodiments, the seizure prediction facility generates a prediction that the patient will experience a seizure at a future time based on the frequency of the PPG pulse increasing, the duration of the PPG pulses decreasing or the area under the curve of the PPG pulses decreasing. In some embodiments, changes in multiple features may be used to predict a future seizure. For example, if the frequency increases, but no other feature changes, the seizure prediction facility may not predict that the patient will experience a seizure, but if the frequency increases and the duration decreases, then the seizure prediction facility may predict that the patient will experience a seizure.

In some embodiments, the change in a feature determined from an analysis of a PPG signal may be combined with one or more other biological indicators obtained from another sensor that may be predictive of a future seizure. For example, the above technique may be combined with techniques that attempt to predict seizures using heart rate variability derived from electrocardiograms, as described in the article by Fujiwara, K., et al., *Epileptic Seizure Prediction Based on Multivariate Statistical Process Control of Heart Rate Variability Features*, published in IEEE Transaction on Biomedical Engineering, Vol. 63, No. 6, June 2016 ("Fujiwara"), which is incorporated herein by reference in its entirety and at least for its discussion of predicting seizures using heart rate variability. (In a case that any terminology used herein conflicts with the usage of that terminology in Fujiwara, the terminology should be afforded a meaning most consistent with how a person of ordinary skill would understand its usage herein). In other embodiments, the above technique may additionally or alternatively be combined with techniques that attempt to predict seizures using temperature data and/or electrodermal activity, as described in International Patent Application PCT/US2016/041085 (Pub. No. WO/2017/007808) entitled SEIZURE PREDICTION BASED ON COMPARISON OF BIOLOGICAL INFORMATION ACROSS WAKE AND SLEEP PERIODS, to Nogueira, A., et al., published Jan. 12, 2017 ("Nogueira"), which is incorporated herein by reference in its entirety and at least for its discussion of the techniques for seizure prediction using temperature data and/or electrodermal activity. (In a case that any terminology used herein conflicts with the usage of that terminology in Nogueira, the terminology should be afforded a meaning most consistent with how a person of ordinary skill would understand its usage herein.) In some embodiments, the other sensor is a non-PPG sensor. For example, the non-PPG sensor may be an electroencephalograph, an electromyograph, an accelerometer, a pulse sensor, a thermometer, an electrodermal activity sensor, or electrocardiograph. The non-PPG sensor may be part of the device that includes the PPG sensor, or the non-PPG sensor may be a separate device that sends data to a common seizure prediction facility.

In some embodiments, the change in at least one fact over time in block 208 may be determined using a neural network that has been trained on a database of previously-collected data. For example, a neural network technique has been proposed for monitoring onset of seizures, using EEG signals, as described in C. Papadelis, et al., "Real-time multi-channel monitoring of burst-suppression using neural network technology during pediatric status epilepticus treatment." Clinical Neurophysiology 2016. 127: p. 28200-2831 ("Papadelis"), which is incorporated herein by reference in its entirety and at least for its discussion of neural network techniques for analyzing EEG signals. (In a case that any terminology used herein conflicts with the usage of that terminology in Papadelis, the terminology should be afforded a meaning most consistent with how a person of ordinary skill would understand its usage herein.) The inventors recognized and appreciated that such neural network techniques may be applied to the types of data and features described herein, to learn relationships between the features described herein and onset of a seizure. For example, the pre-processing and feature extraction discussed above in connection with FIG. 2 (and associated figures) may be performed to generate a set of features from blood volume data that is associated with known occurrences of seizure onset and known times that seizures did not occur. The set of features and associated indications of whether a seizure occurred or did not occur may form at least a part of a labeled set that is input to the neural network to train the neural network. The neural network may then be used to generate the change over time of block 208 and/or the prediction of block 210. As another example, raw data (without the pre-processing or feature extraction) may be input to the neural network together with the known occurrences of seizure onset and known times that seizures did not occur, as a labeled set to train the neural network. As another example, blood volume data (either or both of raw data without the pre-processing or feature extraction or features generated by the pre-processing and feature extraction) may be input to the neural network together with associated times at which the blood volume data was collected from individual patients and information on whether the individual patients experienced a seizure within a time following the collection, to be used in an unsupervised training of the neural network. Once the neural network is trained, new blood volume signal data for a patient, that matches the type of blood volume signal data used in a training of the neural network (e.g., either raw data or extracted features, or both) is input to the neural network, is input to the neural network to generate a prediction of whether the patient will experience a seizure within a subsequent time period. In embodiments in which such a trained neural network is used, the neural network may be implemented in any suitable location within the system of FIG. 1, including within the seizure prediction facility (e.g., within a wearable device 104), on an associated mobile device 106, on a server 110, or in any other suitable location. If the neural network is implemented outside of the wearable device 104 or device 106, blood volume signal data may be transmitted to the neural network and a prediction may be passed back to the wearable device 104 or device 106, for presentation in block 212.

In block 212, the seizure prediction facility outputs the prediction for presentation to the patient and/or a caregiver of the patient. The prediction may be output directly via a user interface of the device on which the seizure detection facility is executing, such as in a case that the seizure prediction facility is executing on a wearable device (e.g., wearable device 104 of FIG. 1) and the wearable device includes a user interface. In other embodiments, the prediction may be output in block 210 by storing the prediction to a storage and/or transmitting the prediction via a network to another device. In a case that the output includes transmission via a network, the prediction may be transmitted via the network to a device including a user interface, such as devices that may be operated by the patient and/or the caregiver (e.g., devices 106, 114 of FIG. 1). The seizure prediction facility may output the prediction along with any other suitable information, such as information regarding the biological characteristic(s) that were analyzed and/or a result of the comparing, or a time period over which the prediction is valid.

Once the prediction is output in block 212, the process 200 ends.

Computer-Implemented Embodiments

Techniques operating according to the principles described herein may be implemented in any suitable manner. Included in the discussion above are a series of flow charts showing the steps and acts of various processes that predict the occurrence of a seizure based on analysis of a blood volume signal. The processing and decision blocks of the flow charts above represent steps and acts that may be included in algorithms that carry out these various processes. Algorithms derived from these processes may be implemented as software integrated with and directing the operation of one or more single- or multi-purpose processors, may be implemented as functionally-equivalent circuits such as a Digital Signal Processing (DSP) circuit or an Application-Specific Integrated Circuit (ASIC), or may be implemented in any other suitable manner. It should be appreciated that the flow charts included herein do not depict the syntax or operation of any particular circuit or of any particular programming language or type of programming language. Rather, the flow charts illustrate the functional information one skilled in the art may use to fabricate circuits or to implement computer software algorithms to perform the processing of a particular apparatus carrying out the types of techniques described herein. It should also be appreciated that, unless otherwise indicated herein, the particular sequence of steps and/or acts described in each flow chart is merely illustrative of the algorithms that may be implemented and can be varied in implementations and embodiments of the principles described herein.

Accordingly, in some embodiments, the techniques described herein may be embodied in computer-executable instructions implemented as software, including as application software, system software, firmware, middleware, embedded code, or any other suitable type of computer code. Such computer-executable instructions may be written using any of a number of suitable programming languages and/or programming or scripting tools, and also may be compiled as executable machine language code or intermediate code that is executed on a framework or virtual machine.

When techniques described herein are embodied as computer-executable instructions, these computer-executable instructions may be implemented in any suitable manner, including as a number of functional facilities, each providing one or more operations to complete execution of algorithms operating according to these techniques. A "functional facility," however instantiated, is a structural component of a computer system that, when integrated with and executed by one or more computers, causes the one or more computers to perform a specific operational role. A functional facility may be a portion of or an entire software element. For example, a functional facility may be implemented as a function of a process, or as a discrete process, or as any other suitable unit of processing. If techniques described herein are implemented as multiple functional facilities, each functional facility may be implemented in its own way; all need not be implemented the same way. Additionally, these functional facilities may be executed in parallel and/or serially, as appropriate, and may pass information between one another using a shared memory on the computer(s) on which they are executing, using a message passing protocol, or in any other suitable way.

Generally, functional facilities include routines, programs, objects, components, data structures, etc. that perform particular tasks or implement particular abstract data types. Typically, the functionality of the functional facilities may be combined or distributed as desired in the systems in which they operate. In some implementations, one or more functional facilities carrying out techniques herein may together form a complete software package. These functional facilities may, in alternative embodiments, be adapted to interact with other, unrelated functional facilities and/or processes, to implement a software program application.

Some example functional facilities have been described herein for carrying out one or more tasks. It should be appreciated, though, that the functional facilities and division of tasks described is merely illustrative of the type of functional facilities that may implement the example techniques described herein, and that embodiments are not limited to being implemented in any specific number, division, or type of functional facilities. In some implementations, all functionality may be implemented in a single functional facility. It should also be appreciated that, in some implementations, some of the functional facilities described herein may be implemented together with or separately from others (i.e., as a single unit or separate units), or some of these functional facilities may not be implemented.

Computer-executable instructions implementing the techniques described herein (when implemented as one or more functional facilities or in any other manner) may, in some embodiments, be encoded on one or more computer-readable media to provide functionality to the media. Computer-readable media include magnetic media such as a hard disk drive, optical media such as a Compact Disk (CD) or a Digital Versatile Disk (DVD), a persistent or non-persistent solid-state memory (e.g., Flash memory, Magnetic RAM, etc.), or any other suitable storage media. Such a computer-readable medium may be implemented in any suitable manner, including as computer-readable storage media 612 of FIG. 6 described below (i.e., as a portion of a computing device 600) or as a stand-alone, separate storage medium. As used herein, "computer-readable media" (also called "computer-readable storage media") refers to tangible storage media. Tangible storage media are non-transitory and have at least one physical, structural component. In a "computer-readable medium," as used herein, at least one physical, structural component has at least one physical property that may be altered in some way during a process of creating the medium with embedded information, a process of recording information thereon, or any other process of encoding the medium with information. For example, a magnetization state of a portion of a physical structure of a computer-readable medium may be altered during a recording process.

In some, but not all, implementations in which the techniques may be embodied as computer-executable instructions, these instructions may be executed on one or more suitable computing device(s) operating in any suitable computer system, including the example computer system of FIG. 1, or one or more computing devices (or one or more processors of one or more computing devices) may be programmed to execute the computer-executable instructions. A computing device or processor may be programmed to execute instructions when the instructions are stored in a manner accessible to the computing device or processor, such as in a data store (e.g., an on-chip cache or instruction register, a computer-readable storage medium accessible via a bus, etc.). Functional facilities comprising these computer-executable instructions may be integrated with and direct the operation of a single multi-purpose programmable digital computing device, a coordinated system of two or more multi-purpose computing device sharing processing power and jointly carrying out the techniques described herein, a single computing device or coordinated system of computing device (co-located or geographically distributed) dedicated to executing the techniques described herein, one or more Field-Programmable Gate Arrays (FPGAs) for carrying out the techniques described herein, or any other suitable system.

Figure 6:
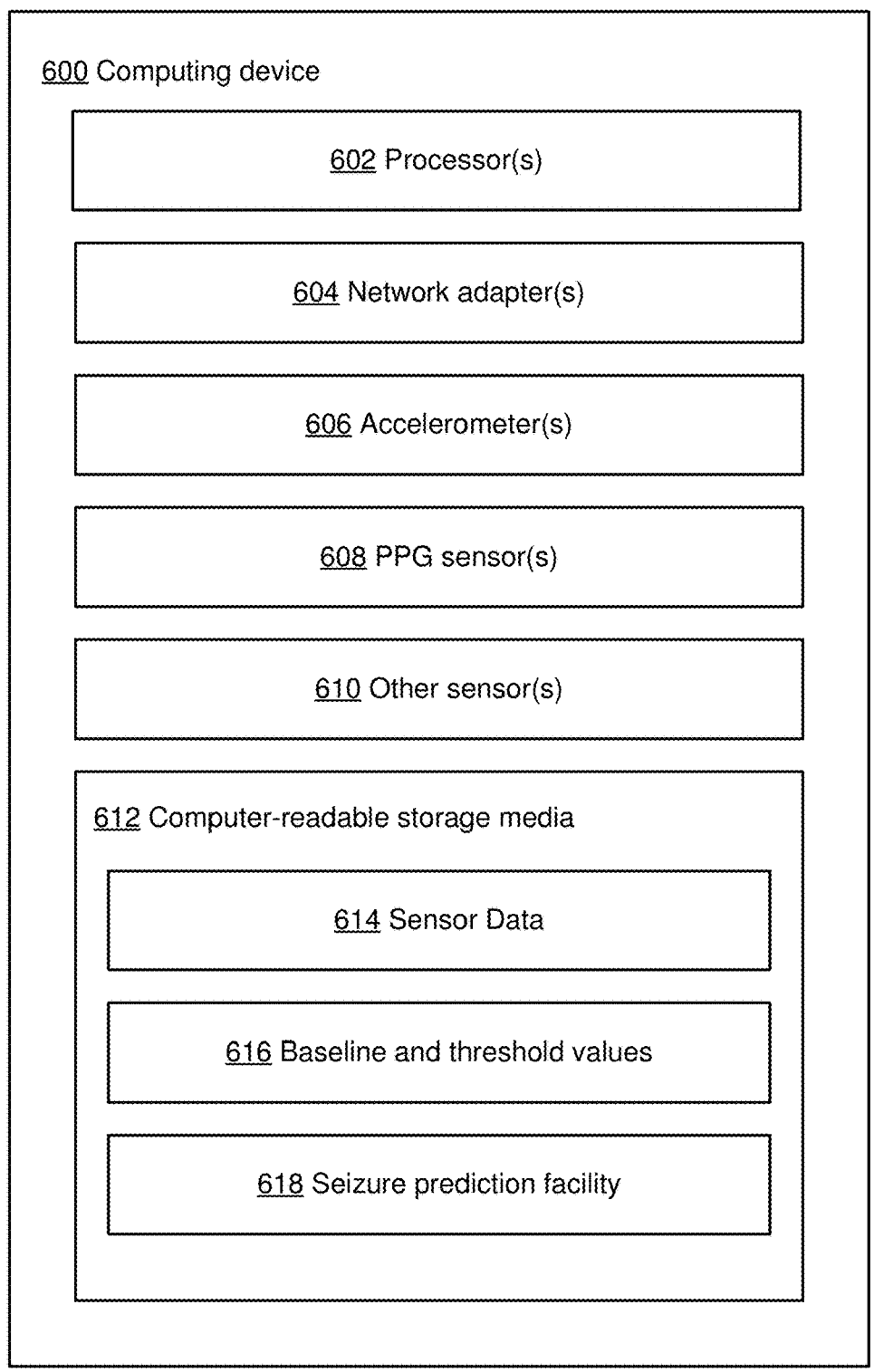
FIG. 6 is a block diagram of an example of a computing device with which some embodiments may operate.

FIG. 6 illustrates one example implementation of a computing device in the form of a computing device 600 that may be used in a system implementing techniques described herein, although others are possible. Computing device 600 may, for example, be implemented as a wearable device, such as device 104 of FIG. 1. It should be appreciated that FIG. 6 is intended neither to be a depiction of necessary components for a computing device to operate as a wearable device 104 or any other computing device of a system operating according to techniques described herein, nor a comprehensive depiction.

Computing device 600 may comprise at least one processor 602, a network adapter 604, and computer-readable storage media 612. Computing device 600 may be, for example, a wearable device, a desktop or laptop personal computer, a personal digital assistant (PDA), a smart mobile phone, a tablet computer, a server, or any other suitable computing device. Network adapter 604 may be any suitable hardware and/or software to enable the computing device 600 to communicate wired and/or wirelessly with any other suitable computing device over any suitable computing network. The computing network may include wireless access points, switches, routers, gateways, and/or other networking equipment as well as any suitable wired and/or wireless communication medium or media for exchanging data between two or more computers, including the Internet. Computer-readable media 612 may be adapted to store data to be processed and/or instructions to be executed by processor 602. Processor 602 enables processing of data and execution of instructions. The data and instructions may be stored on the computer-readable storage media 612 and may, for example, enable communication between components of the computing device 600.

Device 600 may, in some embodiments (e.g., embodiments in which the device 600 is a wearable device), include one or more sensors to measure biological characteristics or other data. In the example of FIG. 6, the device 600 includes one or more accelerometers 606, one or more PPG sensors 608, and one or more other sensors 610, which may include, for example, an electrodermal activity (EDA) sensors, a thermometer, or an electrocardiogram (EKG) sensor.

The data and instructions stored on computer-readable storage media 612 may comprise computer-executable instructions implementing techniques which operate according to the principles described herein. In the example of FIG. 6, computer-readable storage media 612 stores computer-executable instructions implementing various facilities and storing various information as described above. Computer-readable storage media 612 may store sensor data 614, such as PPG signal data, acceleration data, or other data from the other sensors 610. The media 612 may further store data 616 on baseline and threshold values. The media 612 may additionally store instructions for a seizure prediction facility 618, which may implement any of the techniques described above for predicting occurrence of a seizure during a time period.

While not illustrated in FIG. 6, a computing device may additionally have one or more components and peripherals, including input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computing device may receive input information through speech recognition or in other audible format.

Experimental Results

Described above are various examples of processes and devices that may be used in embodiments for seizure prediction. An example of patients with which these devices and techniques may be used is described below to provide a detailed example of how techniques described herein may be used to generate predictions of seizures for patients.

SAS software, version 9.4 Proc Mixed (Cary, N.C.) was used for statistical analysis. All the analyses for individual PPG signal features were carried out using a linear mixed-effect model with random-intercept to account for correlation with-in subjects and variability between subjects under the missing at random (MAR) assumption. Contrasts were constructed to compare the pairwise differences among the various periods. The final model selection was performed using Akaike's Information criterion (AIC). The Benjamini-Hochberg false discovery rate procedure was also applied in order to control for multiple comparisons across all the features and periods.

Of the 108 patients admitted to the epilepsy monitoring unit at Boston Children's Hospital between February 2015 and June 2016, 153 nights of data (72 patients were enrolled for one night, 21 patients were enrolled for two nights, 12 patients were enrolled for three nights and 3 patients were enrolled for four nights) were recorded and 31 patients experienced a seizure during their EEG monitoring time while wearing a wristband-based sensors, the wristbands (E4, Empatica, Milan, Italy) record four modalities: PPG, electrodermal skin response (EDA), skin temperature and three-axis accelerometry. Patients were excluded from the study if they had a vagal nerve stimulator, a cardiac pacemaker, a heart condition susceptible to tiny electrical pulses, a history of cardiac arrhythmia or other independent diseases of the autonomic nervous system, sensitive skin (premature newborns), a history of allergy to rubber or to materials like rubber, or an intolerability to the sensory stimulation of wearing a device. Recorded signals were processed and correlated with seizures detected by video EEG monitoring. The video EEG reading and seizure marking were performed independently from this study by the patients' attending epileptologist. Only patients who had GTC seizures with either primary generalized onset or focal onset with secondary generalization were included in the study. Patients whose recorded PPG signals were affected by major movement artifacts were excluded because the movement impeded analyzing PPG alterations in any of the three investigated phases. Patients whose primary or secondary generalized seizures produced quality PPG signals were included. For each patient, only the first recorded episode of GTC was considered. If a patient had multiple GTCs during their monitoring, only the first episode was included in the analysis.

For each patient, the PPG signals were analyzed during two separate days. To gather peri-ictal signals, PPG signals were examined related to a GTC on a "seizure day." To gather control signals, PPG signals were analyzed on a "seizure-free" day. For peri-ictal signals, three time periods were defined related to seizure progression:

(i) baseline period: from thirty minutes to five hours before the seizure onset;

(ii) pre-seizure period: five-minute period immediately preceding seizure onset;

(iii) post-seizure period: the first hour after seizure termination.

Besides analyzing the signals within the aforementioned seizure-related periods, signals were analyzed from a seizure-free period to distinguish normal changes in PPG signals from changes that are triggered by seizure occurrence. Seizure-free signals were selected for each patient with at least 6 hours distance from the closest seizure onset. Five seizure-free portions were randomly selected for each patient. In-house software developed in MATLAB (MathWorks Inc.) was used for pre-processing, segmentation and feature extraction of the PPG signals.

Seizure onset and offset was defined as the seizure onset and offset recorded by continuous video EEG monitoring. Postictal generalized electroencephalographic suppression (PGES) was defined as the postictal suppression of EEG more than 10 µV and within the immediate 30 seconds after the seizure termination on EEG. An epileptologist reviewed the EEGs and marked the onset and offset of seizures, as well as the presence and duration of PGES.

As discussed above, the PPG signal can be affected by any significant motion of the wristband relative to the limb on which it is worn. The segments of the recordings which were free from motion artifacts were preserved. The data acquired by the three-axis accelerometer were used to detect motions. The accelerometer data was visually inspected and any segment of the recording where motions were found was excluded. Artifact-free segments of at least 62 seconds, 61 seconds, and 75 seconds of duration were selected for baseline, pre-seizure and post-seizure periods, respectively.

Eighteen generalized tonic-clonic (GTC) (primary or secondary generalized) seizure episodes were recorded from eleven patients and the data was analyzed for the first recorded episode of GTC for each of these patients. Demographic characteristics, the age of epilepsy onset, epilepsy type, EEG findings, and MRI features for these eleven patients are depicted in Table 1. In six patients, seizures occurred out of sleep. In five patients, seizures were associated with PGES (Table 1).

TABLE 1

| | | | | | | | |
|---|---|---|---|---|---|---|---|
| Clinical information from 11 patients with GTC | | | | | | | |
| Patient No. | Age (years) | Age at seizure onset/Gender | Epilepsy diagnosis | Ictal EEG findings | State of wakefulness before seizure onset | PGES | MRI findings |
| 1 | 14 | 7 years/Female | Focal epilepsy | Rt central onset FBG | Asleep | Yes | Rt hemisphere infarct |
| 2 | 11 | 9 years/Female | Focal epilepsy | Rt frontal onset FBG | Asleep | Yes | Rt hemisphere infarct |
| 3 | 12 | 14 months/Female | Focal epilepsy | Lt frontal onset FBG | Asleep | Yes | Lt frontal cortical malformation |
| 4 | 12 | 9 years/Male | Focal epilepsy | Rt lateral temporal onset FBG | Asleep | No | Nl MRI (No etiology for epilepsy) |
| 5 | 15 | 13 years/Male | Focal epilepsy | Rt central onset FBG | Awake | No | Malformation of cortical development |
| 6 | 14 | 6 years/Female | Focal epilepsy | Lt central onset FBG | Awake | No | No etiology for epilepsy (Chiari I malformation) |
| 7 | 17 | 15 years/Male | Focal epilepsy | Lt parieto-temporal onset FBG | Awake | Yes | Lt temporal lobe tumor s/p resection |
| 8 | 16 | 15 years/Female | Focal epilepsy | Lt temporal onset FBG | Awake | No | Nl MRI (no etiology for epilepsy) |
| 9 | 22 | 10 years/Female | Focal epilepsy | Lt centro-parietal onset FBG | Asleep | Yes | Lt hemisphere infarct |
| 10 | 9 | 7 years/Male | Focal epilepsy | Rt fronto-central onset FBG | Asleep | No | Lt cortical malformation |

TABLE 1-continued

Clinical information from 11 patients with GTC

| Patient No. | Age (years) | Age at seizure onset/Gender | Epilepsy diagnosis | Ictal EEG findings | State of wakefulness before seizure onset | PGES | MRI findings |
|---|---|---|---|---|---|---|---|
| 11 | 27 | 14 years/ Female | Generalized epilepsy | Generalized onset | Awake | No | Nl MRI (no etiology for epilepsy) |

*Rt: Right,
Lt: Left,
FBG: Followed By Generalization,
Nl: Normal,

From the eleven patients, seven had artifact-free PPG signals during another seizure-free day (control signals), thus for each of them, five portions of signal were selected during seizure-free period. Portions were at least four minutes apart from each other (from the end of one portion to the start time of the following one). Selection of control portions for analysis were performed randomly for five patients and manually for 2 patients (due to limited number of available portions). The duration of PPG signals in addition to the number of PPG pulses selected for analysis for each patient are presented in Table 2.

TABLE 2

Duration and number of PPG pulses selected for analysis from each patient

| | Baseline | | Pre-seizure | | Post-seizure | | |
|---|---|---|---|---|---|---|---|
| ID | Duration (seconds) | Number of PPG pulses | Duration (seconds) | Number of PPG pulses | Duration (seconds) | Number of PPG pulses | Control Duration (seconds) |
| 1 | 61 s | 108 | 85 s | 147 | 119 s | 214 | 408 |
| 2 | 125 s | 152 | 119 s | 139 | 107 s | 158 | 884 |
| 3 | 131 s | 180 | 165 s | 233 | 112 s | 186 | 387 |
| 4 | 84 s | 122 | 213 s | 206 | — | — | — |
| 5 | 104 s | 122 | — | — | 73 s | 103 | 240 |
| 6 | 105 s | 135 | — | — | 98 s | 158 | 241 |
| 7 | 82 s | 109 | — | — | 114 s | 157 | 572 |
| 8 | 402 s | 375 | 59 s | 68 | 100 s | 198 | 300 |
| 9 | 105 s | 96 | 146 s | 107 | 739 s | 954 | — |
| 10 | 269 s | 304 | 296 s | 335 | 815 s | 1195 | — |
| 11 | 155 s | 191 | 78 s | 106 | 232 s | 345 | — |
| Total | 1623 | 1894 | 1161 | 1341 | 2509 | 3668 | 3032 |

Comparison of peri-ictal signals showed significant changes from baseline to both pre- and post-seizure periods for the following features: frequency, peak amplitude, duration, increasing slope, decreasing slope, smoothness and area under the curve. As shown in Table 3, peak amplitude, duration, slope, smoothness, and area under the curve changed significantly from baseline to the pre-seizure period, and also from baseline to post-seizure periods. These findings result from the analysis of data from 11 patients with GTC.

TABLE 3

Results of comparing signal features in baseline vs. pre and post-seizure phases in 11 patients

| Feature | Phase | Estimate | 95% CI | P value |
|---|---|---|---|---|
| Frequency | Baseline vs. pre-seizure | −0.01287 | (−0.02921, 0.003468) | 0.1226 |
| | Baseline vs. post-seizure | 0.3553 | (0.3421, 0.3686) | <0.0001 |
| Peak amplitude | Baseline vs. pre-seizure | 31.3804 | (28.5518, 34.209) | <0.0001 |
| | Baseline vs. post-seizure | 14.1381 | (11.8416, 16.4346) | <0.0001 |
| Duration | Baseline vs. pre-seizure | 0.02698 | (0.0173, 0.03667) | <0.0001 |
| | Baseline vs. post-seizure | −0.2042 | (−0.2121, −0.1964) | <0.0001 |

TABLE 3-continued

Results of comparing signal features in baseline vs. pre and post-seizure phases in 11 patients

| Feature | Phase | Estimate | 95% CI | P value |
|---|---|---|---|---|
| Increasing slope | Baseline vs. pre-seizure | 135.68 | (122.27, 149.09) | <0.0001 |
| | Baseline vs. post-seizure | 98.1731 | (87.2862, 109.06) | <0.0001 |
| Decreasing slope | Baseline vs. pre-seizure | 53.5112 | (48.509, 58.5134) | <0.0001 |
| | Baseline vs. post-seizure | 92.3224 | (88.2612, 96.3836) | <0.0001 |
| Smoothness | Baseline vs. pre-seizure | 0.02331 | (0.005357, 0.04125) | 0.0109 |
| | Baseline vs. post-seizure | 0.2557 | (0.2412, 0.2703) | <0.0001 |
| Area under the curve | Baseline vs. pre-seizure | 15.7617 | (14.3018, 17.2217) | <0.0001 |
| | Baseline vs. post-seizure | −5.7356 | (−6.9209, −4.5502) | <0.0001 |

FIGS. 7A, 7B, 7C, 7D, 7E, 7F, and 7G include comparisons of changes during seizure-free (control) periods with changes during post-seizure and pre-seizure periods for the various features extracted from the PPG signals. Plot 710 shows the results for the frequency; plot 720 shows the results for the peak amplitude; plot 730 shows the results for the pulse duration; plot 740 shows the results for the increasing slope; plot 750 shows the results for the decreasing slope; plot 760 shows the results for the smoothness; and plot 770 shows the results for the area under the curve (AUC). The data bars in the plots of FIGS. 7A, 7B, 7C, 7D, 7E, 7F, and 7G represent the mean estimate of change with error bars representing the 95% confidence interval around the mean. P values are shown above the data pars, where a single asterisk (*) represent p value<0.0001 and two asterisks (**) represents a p value<0.05. The first five bars represent the difference between the feature in a pre-seizure time period and five different control periods. The middle 10 bars represent the difference between various control periods. The final five bars represent the difference between the feature in a post-seizure time period and the five different control periods. Analysis of control signals during seizure-free days showed significant results for most of the observations. In other words, PPG signals depicted changes even without a seizure trigger.

FIGS. 8A, 8B, 8C, 8D, 8E, 8F, and 8G illustrate the changing pattern for each signal feature during seizure-free periods as well as during pre-seizure and post-seizure periods. Plot 810 shows the mean estimate for the frequency during seizure-free (control) periods, pre-seizure periods and post-seizure periods; plot 820 shows the mean estimate for the peak amplitude during seizure-free (control) periods, pre-seizure periods and post-seizure periods; plot 830 shows the mean estimate for the pulse duration during seizure-free (control) periods, pre-seizure periods and post-seizure periods; plot 840 shows the mean estimate for the increasing slope during seizure-free (control) periods, pre-seizure periods and post-seizure periods; plot 850 shows the mean estimate for the decreasing slope during seizure-free (control) periods, pre-seizure periods and post-seizure periods; plot 860 shows the mean estimate for the smoothness during seizure-free (control) periods, pre-seizure periods and post-seizure periods; and plot 870 shows the mean estimate for the area under the curve (AUC) during seizure-free (control) periods, pre-seizure periods and post-seizure periods. The data bars in FIGS. 8A, 8B, 8C, 8D, 8E, 8F, and 8G represent the mean estimate with error bars representing the 95% confidence interval around the mean. The first five bars in each plot of FIGS. 8A, 8B, 8C, 8D, 8E, 8F, and 8G represent the mean estimate for five different control periods. The middle sixth bar in each plot represents the mean estimate during a pre-seizure time period. The seventh and final bar of each plot represent the mean estimate for a post-seizure time period.

To compare the above changes with the changes around seizure occurrence, the magnitude and consistency of the changes in FIGS. 7A, 7B, 7C, 7D, 7E, 7F, and 7G include were investigated. In FIGS. 7A, 7B, 7C, 7D, 7E, 7F, and 7G include, all the changes are presented with a positive sign for better visualization although not all of the results were positive. Results of these comparisons are reported in two categories: Pre-seizure vs. Control and Post-seizure vs. Control.

Figure 7A:
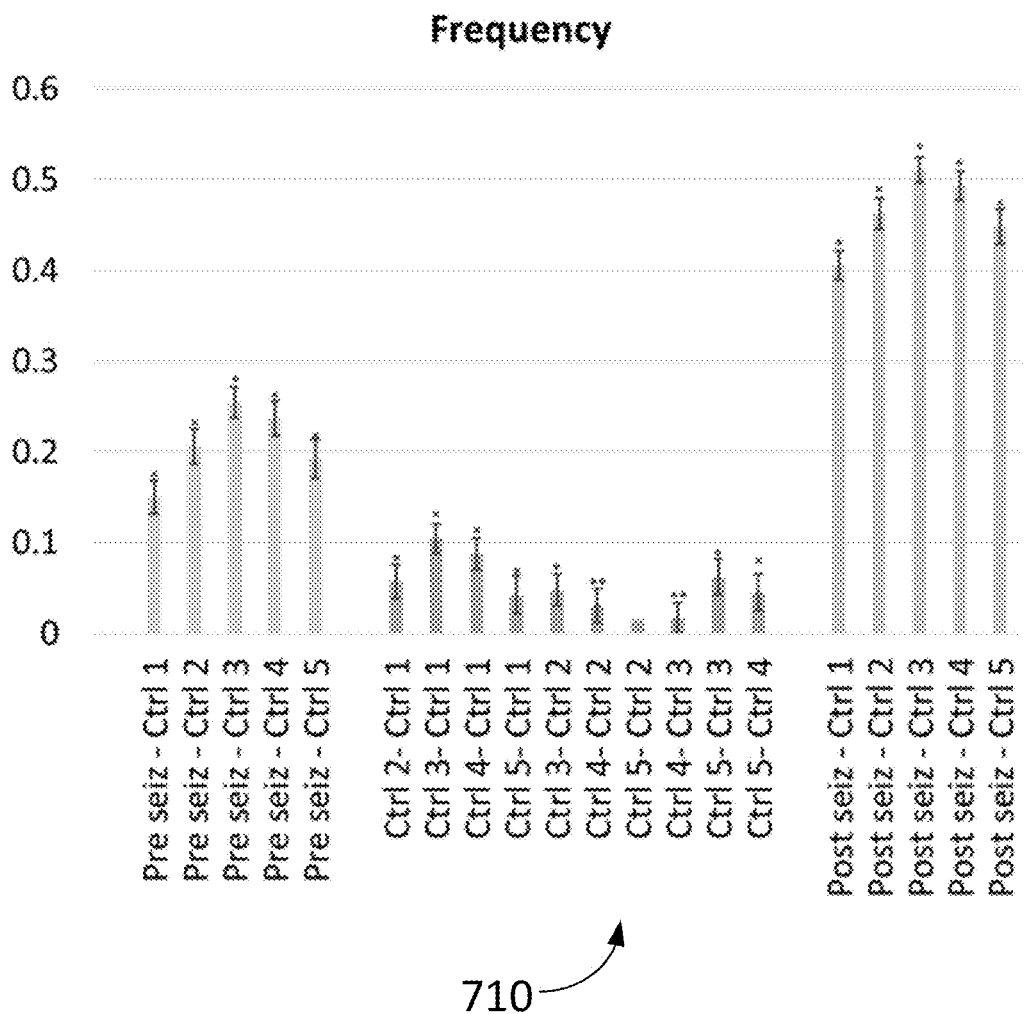
FIGS. 7A, 7B, 7C, 7D, 7E, 7F, and 7G include plots of the changes of various features extracted from a blood volume signal during seizure-free periods, post-seizure periods, and pre-seizure periods.
Figure 8A:
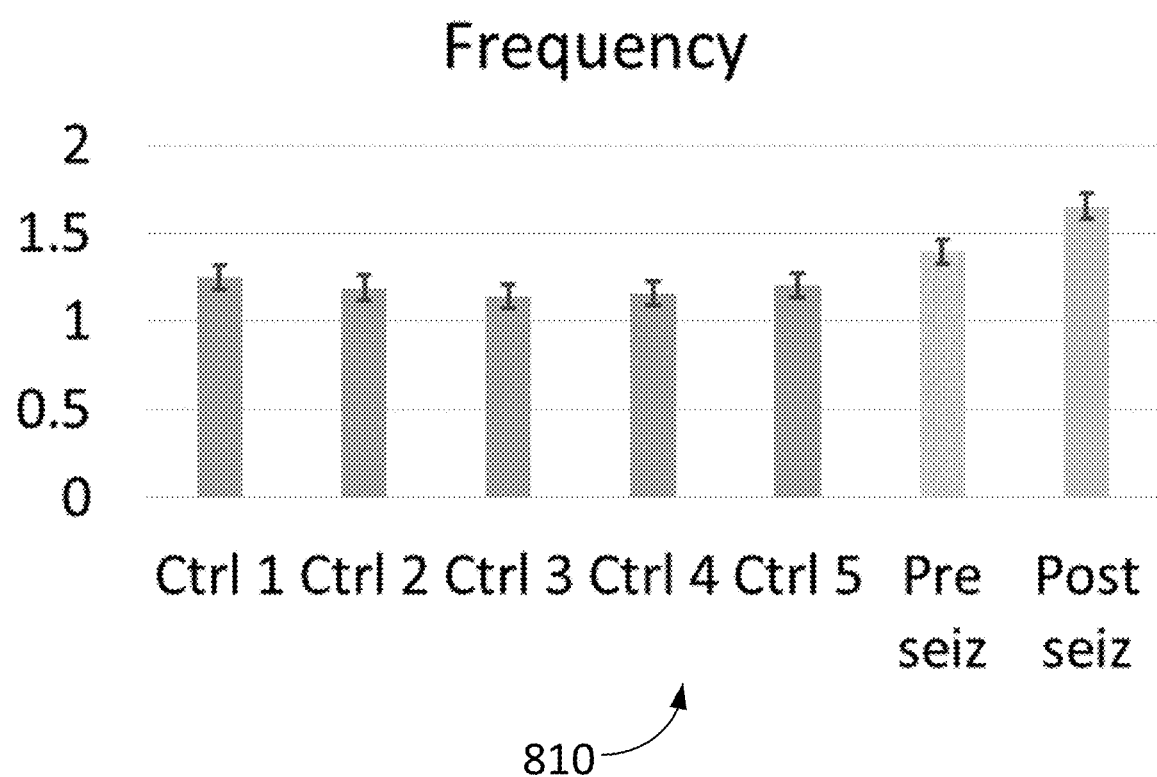
FIGS. 8A, 8B, 8C, 8D, 8E, 8F, and 8G include plots of the changing pattern of various features extracted from a blood volume signal during seizure-free periods, post-seizure periods, and pre-seizure periods.

Pre-Seizure vs. Control:

Frequency:

The results showed that frequency increased consistently (FIG. 8A, Plot 810) and significantly during pre-seizure period compared to control segments (p<0.0001, FIG. 7A, Plot 710). The average increase in pre-seizure frequency was 0.20 Hz. Significant changes in frequency were also found among control segments; however, the change in frequency in the control segments was consistently lower (0.05 Hz) than the change occurring during the pre-seizure period.

Figure 7B:
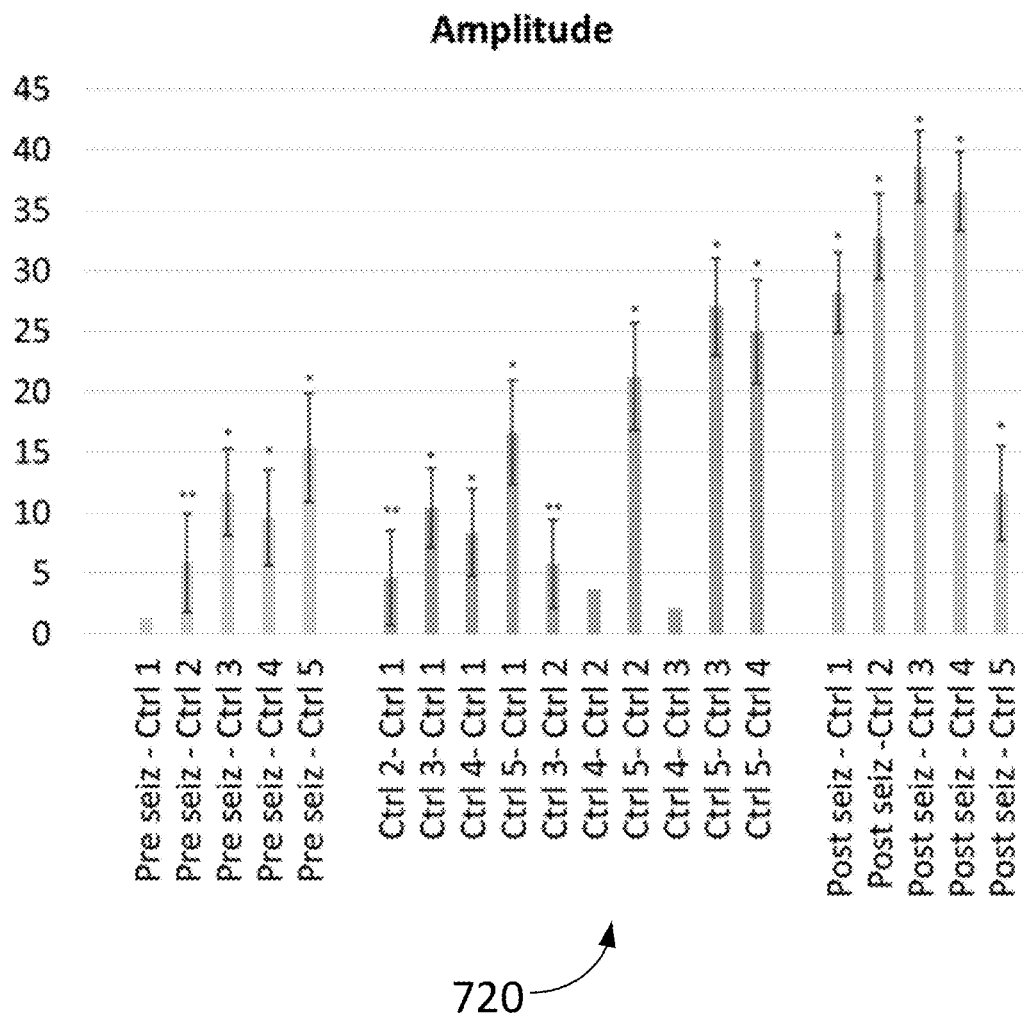
Figure 8B:
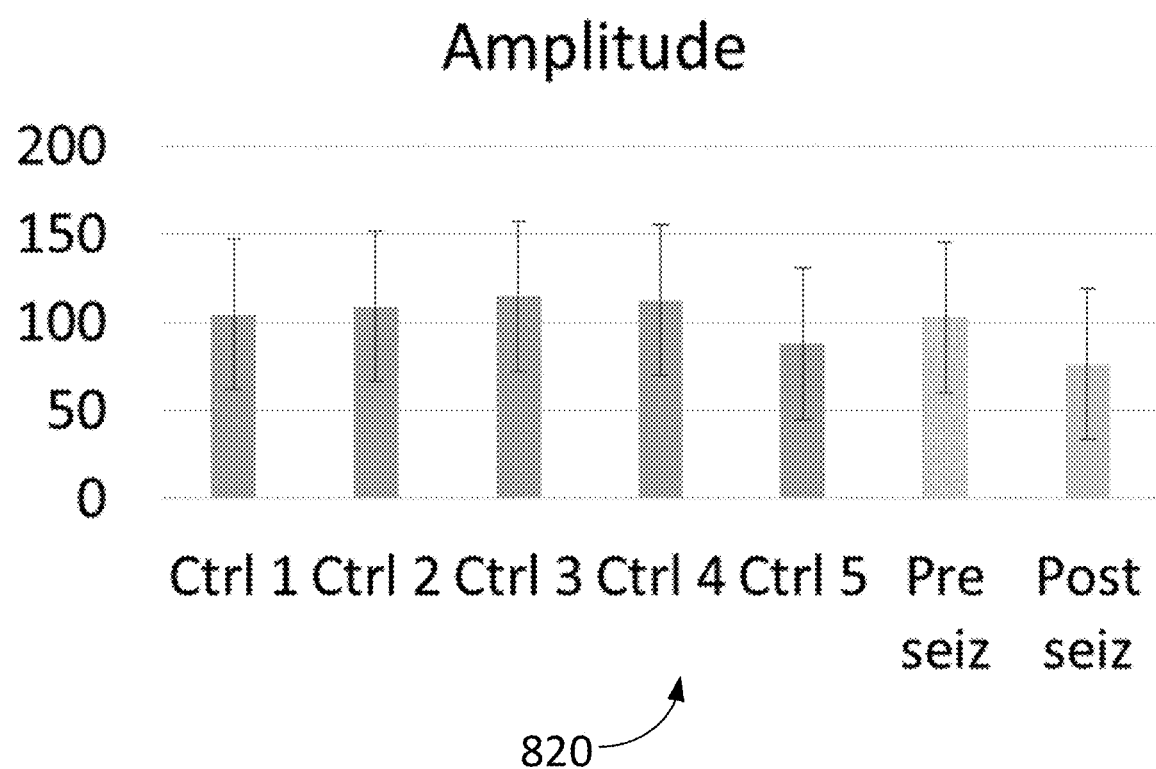

Amplitude:

The results showed that changes in amplitude are not consistent during the pre-seizure period. Namely, comparing pre-seizure amplitude with 5 control portions, showed decrease for four comparisons and increase for the other one (FIG. 8B, Plot 820). The magnitude of changes during pre-seizure period was overlapping with changes during the control portions (FIG. 7B, Plot 720).

Figure 7C:
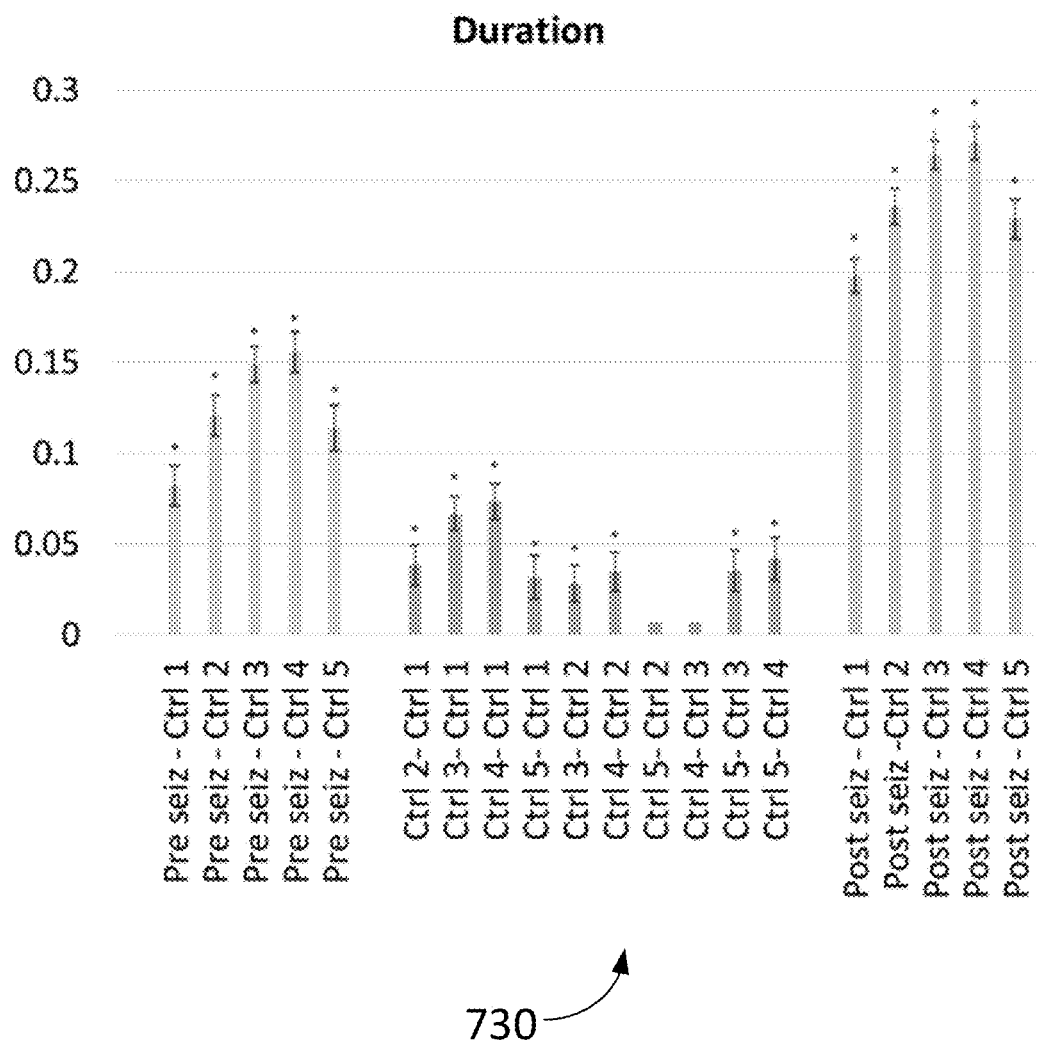
Figure 8C:
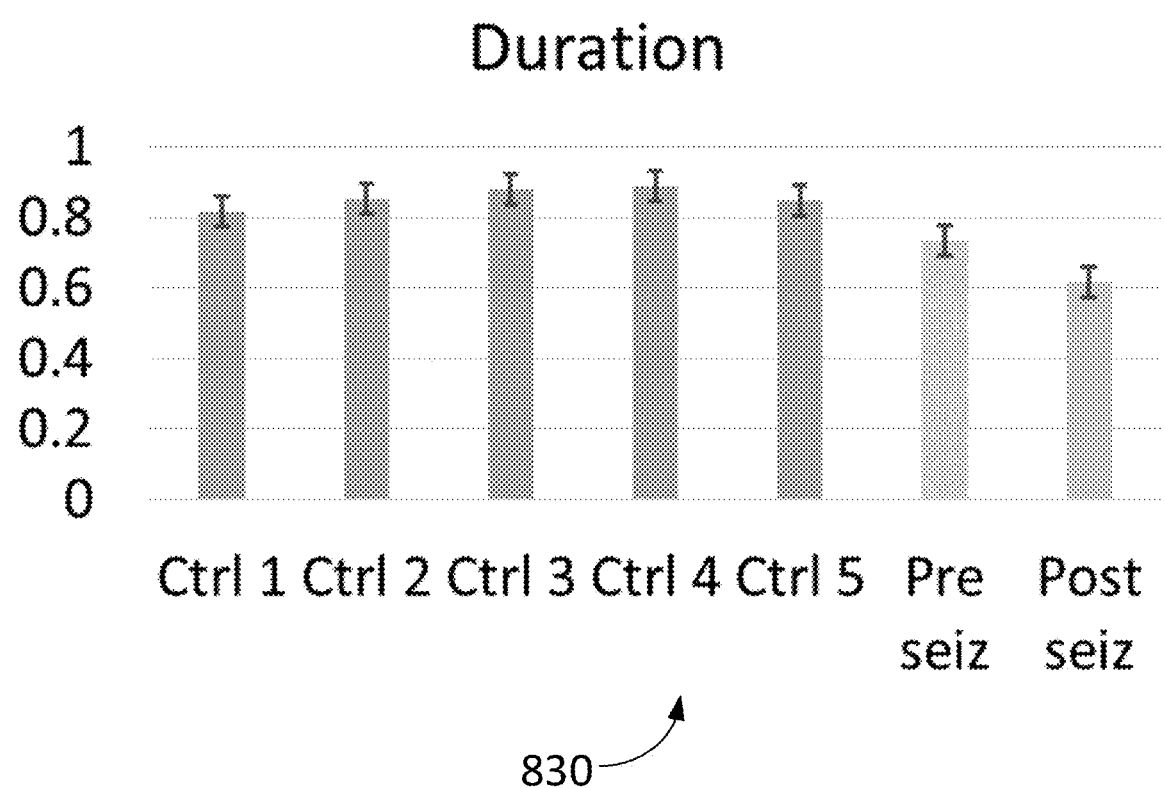

Duration:

Duration of PPG pulses decreased consistently (FIG. 8C, Plot 830) and significantly during pre-seizure period compared to control portions (p<0.0001, FIG. 7C, Plot 730). The mean decrease in pre-seizure duration was 0.12 seconds which was higher compared to average changes during control segments (0.04 s).

Figure 7D:
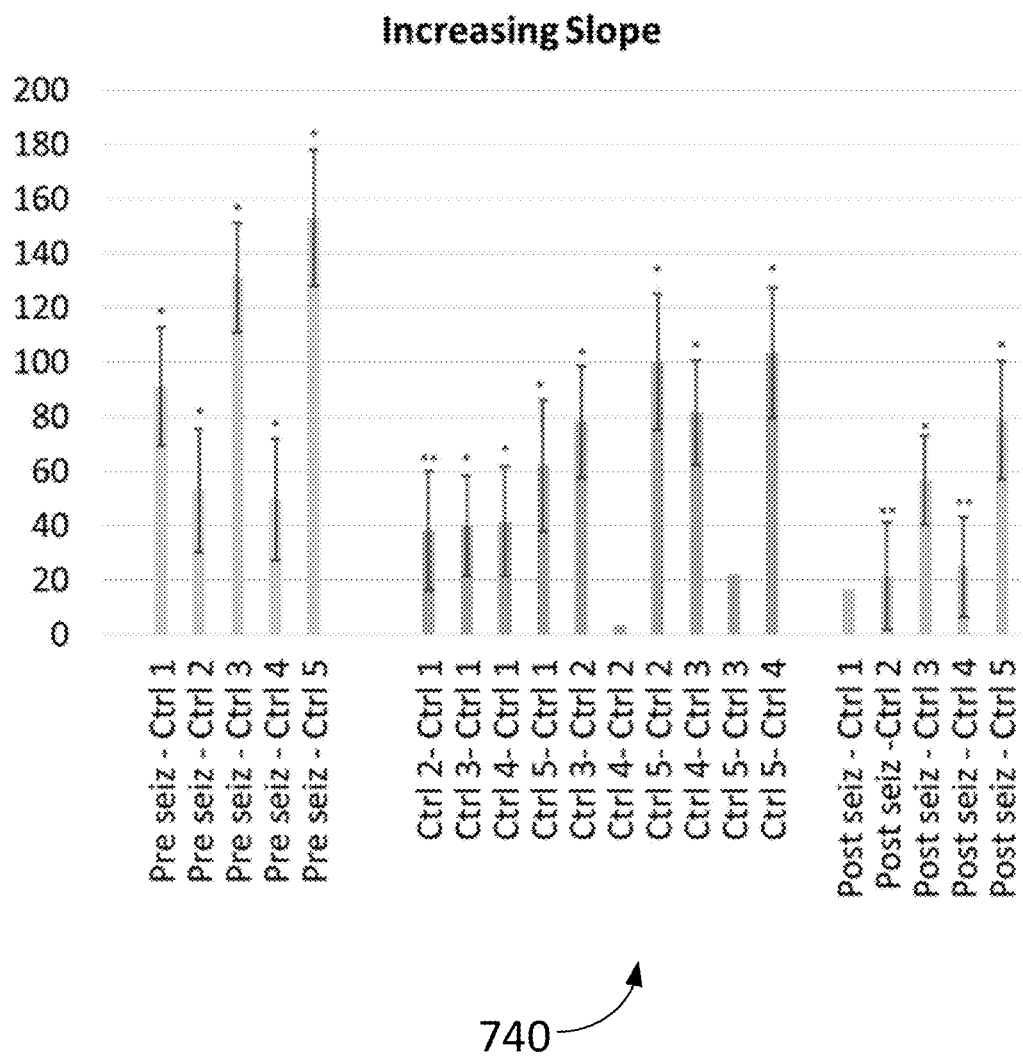

Increasing Slope:

FIG. 4, Plot 840 shows a consistent pattern of increase for increasing slope during pre-seizure period. The comparisons showed an average 95 nW/sec increase in slope during pre-seizure period, which is close to mean changes during control portions (68 nW/sec) and the overlap is shown in FIG. 7D, Plot 740.

Figure 7E:
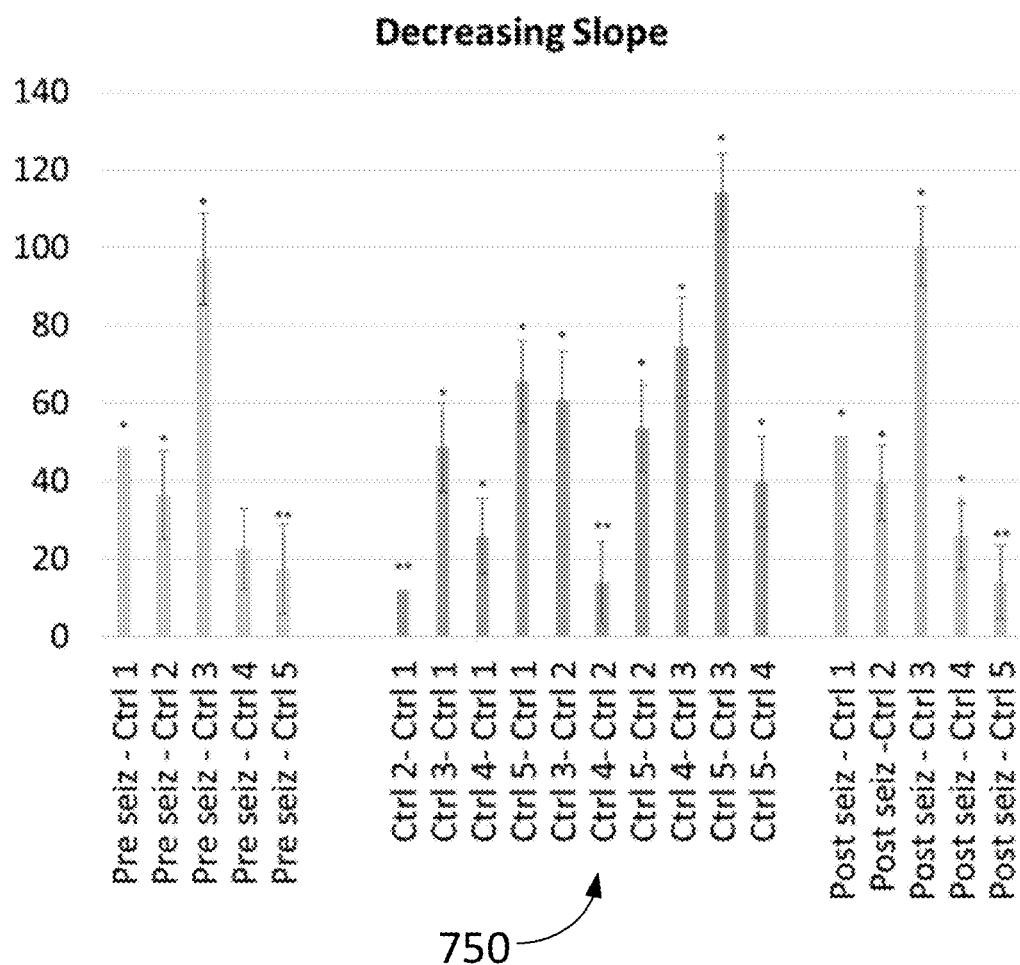
Figure 8D:
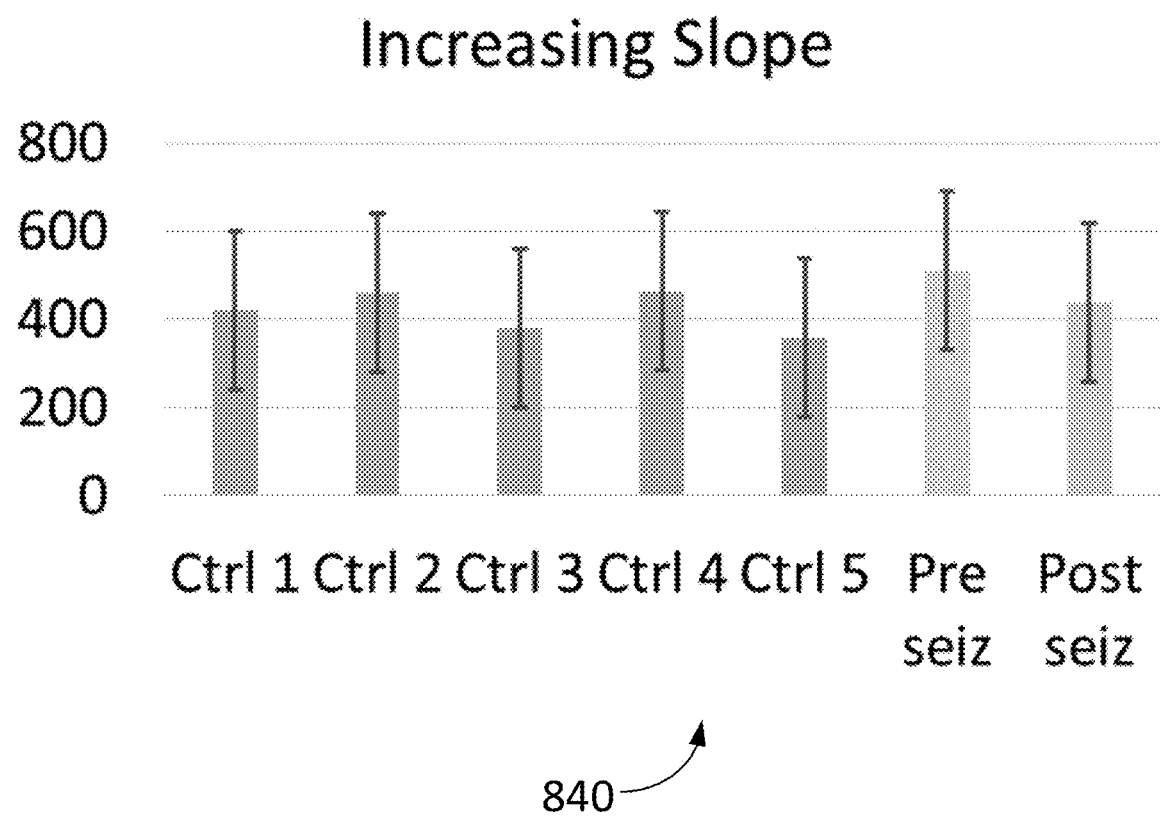
Figure 8E:
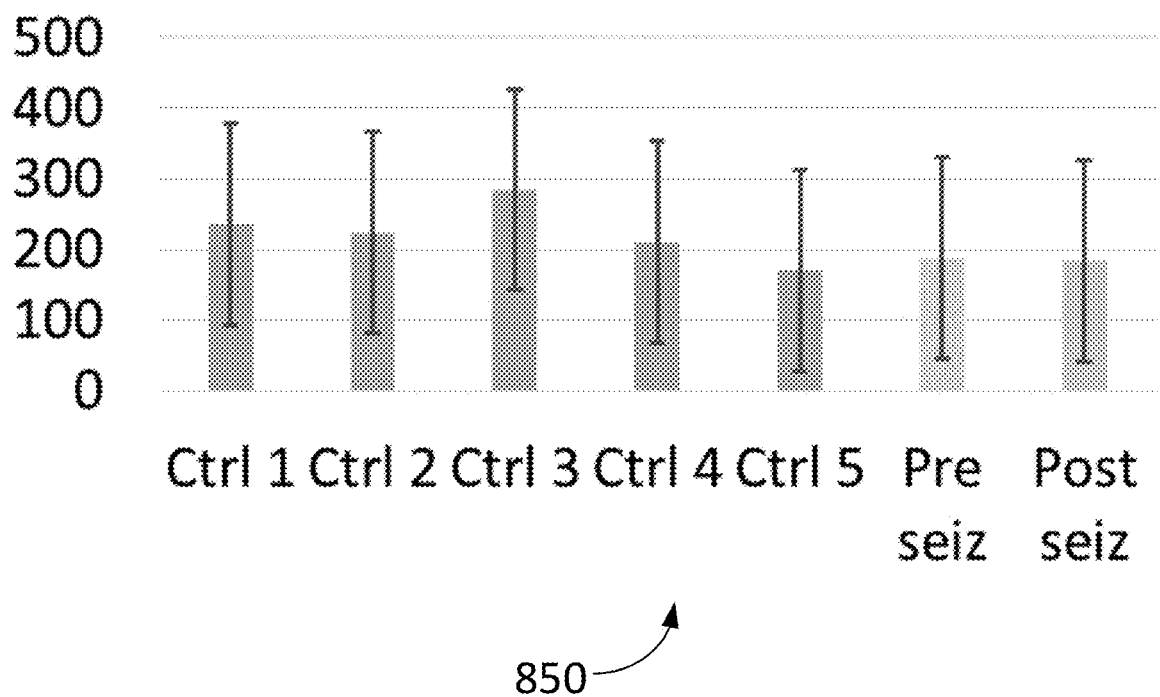

Decreasing Slope:

The results show that decreasing slope did not have any consistent pattern of change during pre-seizure period (FIG. 8E, Plot 850). On the other hand, although the comparisons show significant changes in decreasing slope compared to control segments, these changes are still overlapping (FIG. 7E, Plot 750).

Figure 7F:
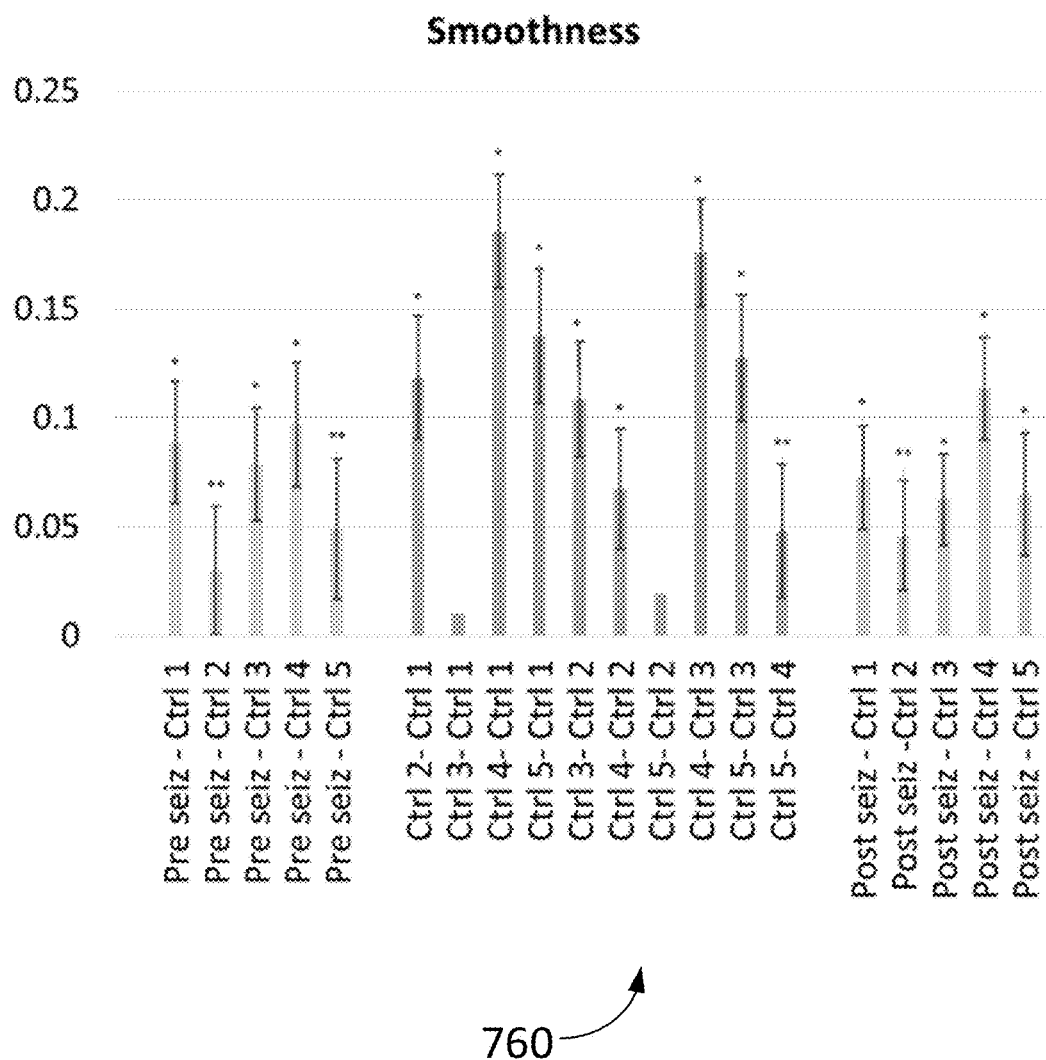
Figure 8F:
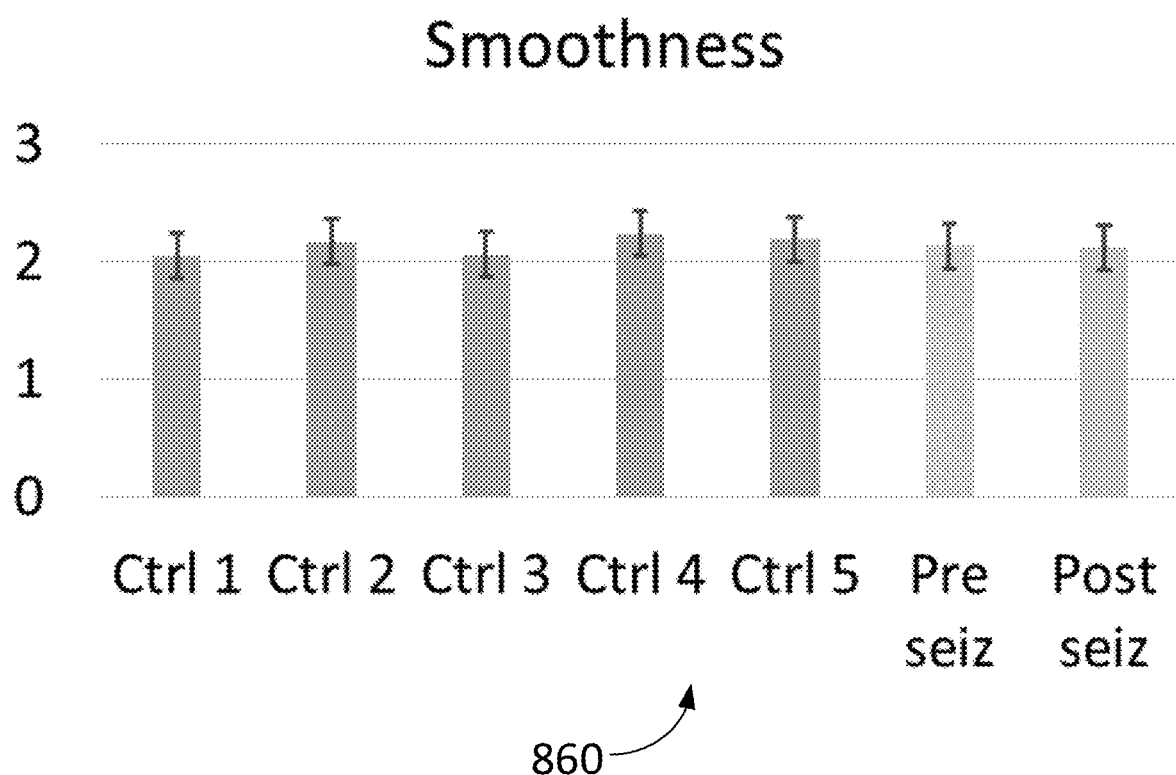

Smoothness:

Smoothness of the PPG pulses did not show any consistent pattern of change during pre-seizure period compared to control portions as shown in FIG. 8F, Plot 860. Although the changes were significant, they were not different from changes during control portions (FIG. 7F, Plot 760).

Figure 7G:
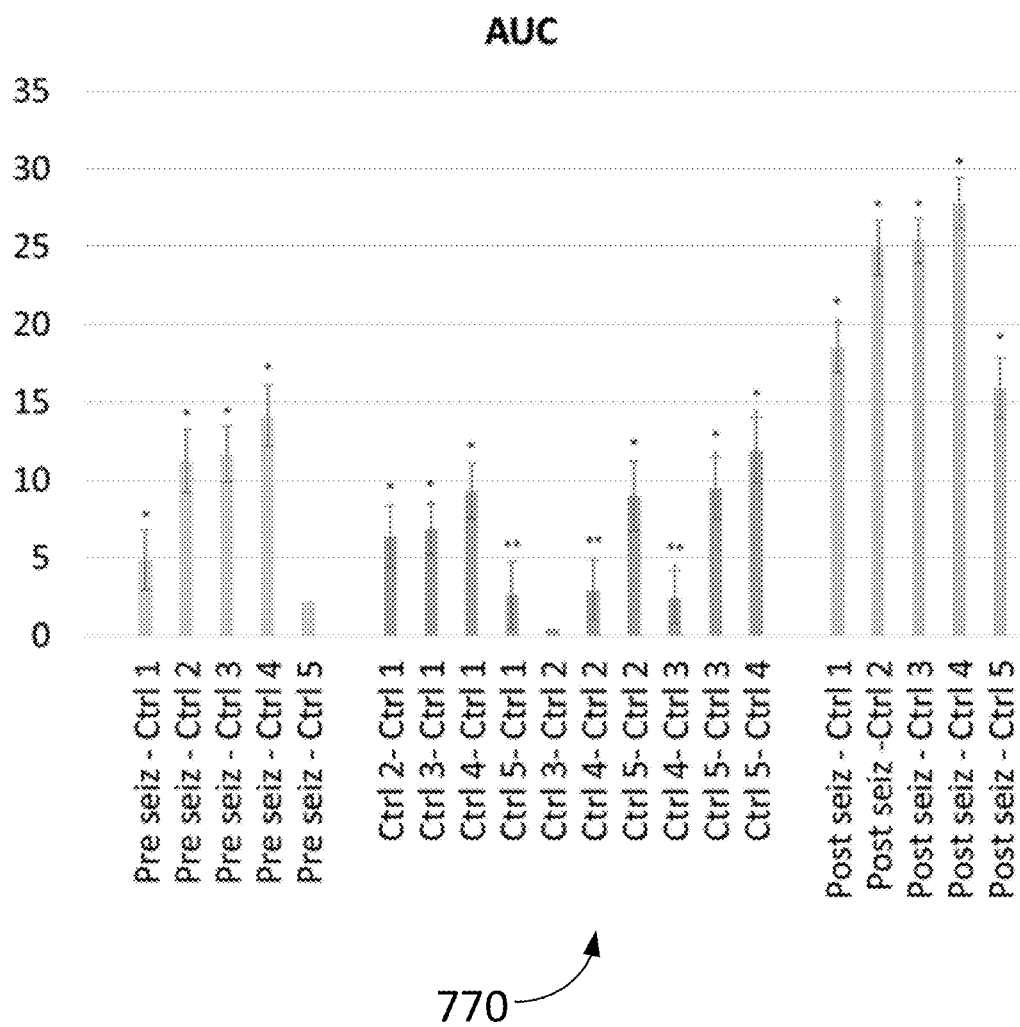
Figure 8G:
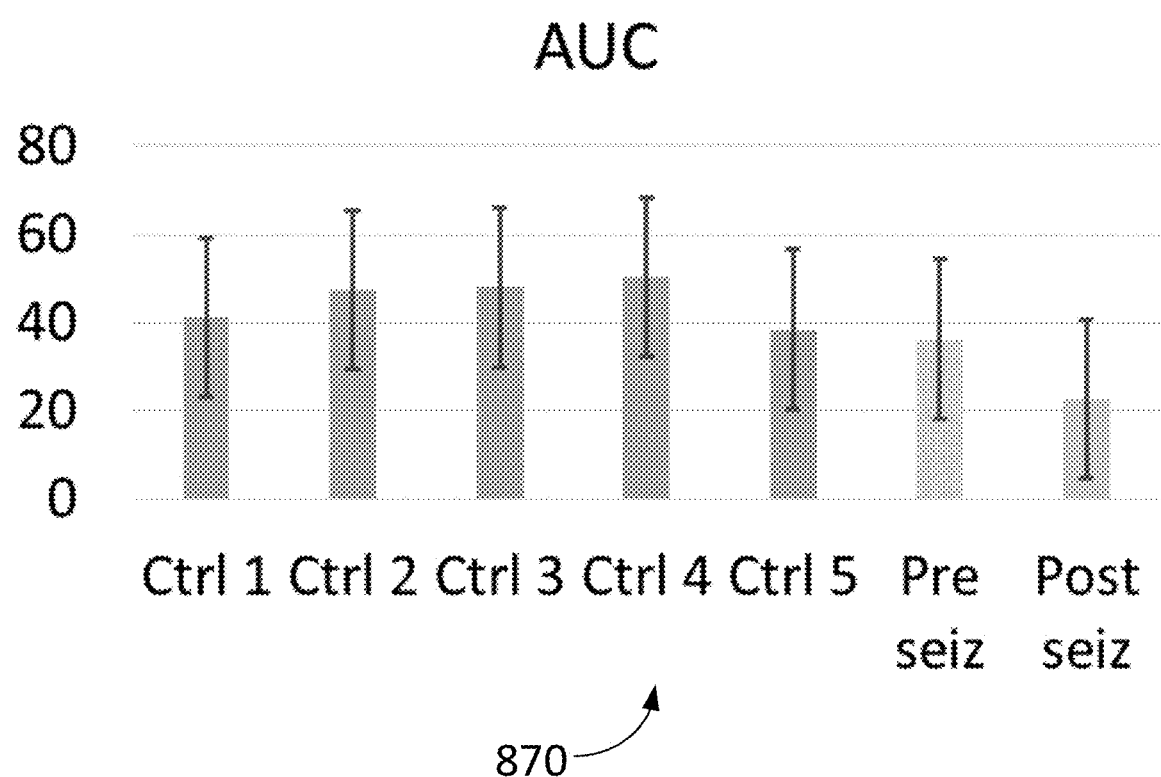

Area Under the Curve (AUC):

Our results show that AUC decreased consistently during the pre-seizure period compared to control portions (FIG. 8G, Plot 870). Although these changes were significant for most of the comparisons, the mean decrease was 10.46 nW·sec during pre-seizure period and 6.76 nW·sec during control portions, which are overlapping as shown in FIG. 7G, Plot 770.

Post-Seizure vs. Control:

Frequency:

The results showed that frequency of PPG pulses increased consistently (FIG. 8A, Plot 810) and significantly during post-seizure period compared to control portions ($p<0.0001$, FIG. 7A, Plot 710). The mean post-seizure increase in frequency was equal to 0.46 Hz, which was higher than the changes during control portions (0.05 Hz) (see FIG. 7A, Plot 710).

Amplitude:

The amplitude of PPG pulse waves decreased consistently during post-seizure period compared to seizure-free periods (FIG. 8B, Plot 820). The mean post-seizure decrease in amplitude was 29.56 nW, compared to the mean change in amplitude during control portions—which was equal to 14.88 nW. As shown in FIG. 7B, Plot 720, these changes are overlapping.

Duration:

The duration of PPG pulse waves decreased consistently during the post-seizure period compared to control portions (FIG. 8C, Plot 830). The average decrease in post-seizure duration of PPG pulses was 0.23 seconds. The duration of PPG pulses showed significant changes during control portions as well, but the mean change was 0.04 seconds which was lower than changes during post-seizure period (FIG. 7C, Plot 730).

Increasing Slope:

The results showed that changes in increasing slope during the post-seizure period compared to the control portions were not consistent (FIG. 8D, Plot 840).

Additionally, the magnitude of changes during post-seizure period were overlapping with changes during control portions (FIG. 7D, Plot 740).

Decreasing Slope:

The results showed that decreasing slope did not change consistently during post-seizure period (FIG. 8E, Plot 850), and the magnitude of changes during post-seizure period were overlapping with changes during control portions (FIG. 7E, Plot 750).

Smoothness:

The smoothness of PPG pulse waves did not show any consistent pattern of change during post-seizure period compared to control portions (FIG. 8F, Plot 860). Additionally, the magnitude of changes during post-seizure period are not different from changes during control portions (FIG. 7F, Plot 760).

Area Under the Curve (AUC):

Our results show that AUC decreased consistently during the post-seizure period compared to control portions (FIG. 8G, Plot 870). These changes were significant for all of the comparisons and the mean decrease in AUC was 22.50 nW·sec, which was higher than the mean change during control portions (6.76 nW·sec) (FIG. 7G, Plot 770).

As illustrated by FIGS. 7A, 7B, 7C, 7D, 7E, 7F, and 7G and FIGS. 8A, 8B, 8C, 8D, 8E, 8F, and 8G the consistency and magnitude of PPG signal changes for frequency, duration, and area under the curve are more prominent during post-seizure and/or pre-seizure period(s) compared to baseline signals. Specifically, frequency and duration changes were more prominent during pre-seizure period. The results, therefore, show that there is a significant change in PPG signals immediately before and after seizure occurrence in patients with epilepsy. Although these changes are also present during seizure-free days, the magnitude of changes are remarkably higher around seizure time compared to seizure-free days and this difference was evident in different features of the PPG signal, such as frequency, duration, and area under the curve.

These results suggest that using non-invasive biosensors to monitor the PPG signals enables seizure detection few minutes before it starts and can alert caregivers when the patient is having an unwitnessed seizure.

Additional Considerations

Embodiments have been described where the techniques are implemented in circuitry and/or computer-executable instructions. It should be appreciated that some embodiments may be in the form of a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Various aspects of the embodiments described above may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

Having thus described several aspects of at least one embodiment, it is to be appreciated that various alterations, modifications, and improvements will readily occur to those skilled in the art. Such alterations, modifications, and improvements are intended to be part of this disclosure, and are intended to be within the spirit and scope of the principles described herein. Accordingly, the foregoing description and drawings are by way of example only.

The invention claimed is:

1. An apparatus comprising:
at least one first sensor to measure blood volume at a location within a patient;
at least one processor; and
at least one storage having encoded thereon executable instructions that, when executed by the at least one processor, cause the at least one processor to perform a method comprising:
monitoring, by the at least one processor, a blood volume signal received from the at least one sensor;
extracting, by the at least one processor, a plurality of features from the blood volume signal at a plurality of times, wherein the plurality of features characterize properties of pulses in the blood volume signal at each time of the plurality of times;

determining, by the at least one processor, a change in the plurality of features over time; and generating, by the at least one processor, a prediction of whether the patient will experience a seizure at a future time based at least in part on a result of the determining; and causing, by the at least one processor, a display associated with the at least one first sensor to produce a notification of the seizure at the future time to warn the patient to mitigate the seizure.

2. The apparatus of claim 1, wherein:
the future time is more than one minute after a time the prediction is generated;
the at least one first sensor is a photoplethysmograph comprising a light source and a photodetector; and
the blood volume signal is obtained from the photodetector of the photoplethysmograph.

3. The apparatus of claim 1, wherein:
the apparatus comprises at least one motion sensor to measure movement of the patient, wherein the motion sensor is an accelerometer worn by the patient;
the method further comprises determining, based on movement signal from the at least one motion sensor, whether the patient moved during a first time period; and
the method further comprises pre-processing the blood volume signal prior to the extracting, wherein the pre-processing comprises excluding a portion of the blood volume signal corresponding to the first time period from the extracting, and wherein the pre-processing comprises filtering the blood volume signal using one or more of a band-pass filter and a Butterworth filter.

4. The apparatus of claim 1, wherein the extracting comprises:
identifying a plurality of individual pulses in the blood volume signal; and
extracting the plurality of features from at least one of individual pulse of the plurality of individual pulses, wherein the at least one feature extracted from the at least one individual pulse comprises one or more of the frequency, the duration, and the area under a curve associated with each pulse.

5. The apparatus of claim 1, wherein the determining the change comprises determining that a difference between the plurality of features and a baseline value is greater than a threshold.

6. The apparatus of claim 5, wherein the baseline value is based at least in part on one or more blood volume measurements made during a time period more than 30 minutes before a current time.

7. The apparatus of claim 5, wherein the threshold is a dynamic threshold based at least in part on one or more blood volume measurements made during a time period more than 30 minutes before the onset of a seizure in the patient.

8. The apparatus of claim 1, wherein:
the apparatus further comprises at least a second sensor to measure a second biological indicator of the patient, wherein the second sensor comprises one or more of an electroencephalograph, an electromyograph, an accelerometer, a pulse sensor, a thermometer, an electrodermal activity sensor, or electrocardiograph; and
the generating the prediction is based at least on the measured second biological indicator.

9. A method comprising:
determining, by the at least one processor, a change in a plurality of features extracted from a photoplethysmography (PPG) measurement of a patient, wherein the plurality of features characterize properties of pulses in the blood volume signal at each time of the plurality of times; and generating, by the at least one processor, a prediction of whether the patient will experience a seizure at a future time based at least in part on a result of the determining; and causing, by the at least one processor, a display associated with at least one first sensor to produce a notification of the seizure at the future time to warn the patient to mitigate the seizure.

10. The method of claim 9, wherein the method further comprises extracting the plurality of features from the PPG measurement, wherein the extracting comprises: identifying a plurality of individual pulses in the blood volume signal; and extracting the at least one feature plurality of features from at least one of individual pulse of the plurality of individual pulses, wherein the at least one feature extracted from the at least one individual pulse comprises one or more of the frequency, the duration, and the area under a curve associated with each pulse.

11. The method of claim 9, wherein the determining the change comprises determining that a difference between the plurality of features and a baseline value is greater than a threshold.

12. The method of claim 11, wherein the baseline value is based at least in part on one or more PPG measurements made during a time period more than 30 minutes before the onset of a seizure in the patient.

13. The method of claim 11, wherein the threshold is a dynamic threshold based at least in part on one or more blood volume measurements made during a time period more than 30 minutes before the onset of a seizure in the patient.

14. The method of claim 9, wherein generating the prediction is based on a multi-modal analysis based on the result of the determining and at least one biological indicator obtained from a non-PPG sensor, wherein the non-PPG sensor comprises one or more of an electroencephalograph, an electromyograph, an accelerometer, a pulse sensor, a thermometer, an electrodermal activity sensor, or electrocardiograph.

15. At least one non-transitory storage medium encoded with executable instructions that, when executed by at least one processor, cause the at least one processor to carry out a method of analyzing data associated with a photoplethysmography (PPG) measurement, wherein the method comprises:
determining, by the at least one processor, a change in a plurality of features extracted from a photoplethysmography (PPG) measurement of a patient, wherein the plurality of features characterize properties of pulses in the blood volume signal at each time of the plurality of times; and generating, by the at least one processor, a prediction of whether the patient will experience a seizure at a future time based at least in part on a result of the determining; and causing, by the at least one processor, a display associated with at least one first sensor to produce a notification of the seizure at the future time to warn the patient to mitigate the seizure.

16. The least one non-transitory storage medium of claim 15, wherein the method further comprises extracting the plurality of features from the PPG measurement, wherein the extracting comprises:
  identifying a plurality of individual pulses in the blood volume signal; and
  extracting the at least one feature from at least one of individual pulse of the plurality of individual pulses, wherein the plurality of features extracted from the at least one individual pulse comprises one or more of the frequency, the duration, and the area under a curve associated with each pulse.

17. The least one non-transitory storage medium of claim 15, wherein the determining the change comprises determining that a difference between the plurality of features and a baseline value is greater than a threshold.

18. The least one non-transitory storage medium of claim 17, wherein the baseline value is based at least in part on one or more PPG measurements made during a time period more than 30 minutes before the onset of a seizure in the patient.

19. The least one non-transitory storage medium of claim 17, wherein the threshold is a dynamic threshold based at least in part on one or more blood volume measurements made during a time period more than 30 minutes before the onset of a seizure in the patient.

20. The least one non-transitory storage medium of claim 15, wherein generating the prediction is based on a multi-modal analysis based on the result of the determining and at least one biological indicator obtained from a non-PPG sensor, wherein the non-PPG sensor comprises one or more of an electroencephalograph, an electromyograph, an accelerometer, a pulse sensor, a thermometer, an electrodermal sensor, or electrocardiograph.

* * * * *